(12) United States Patent
Fitch et al.

(10) Patent No.: US 7,897,612 B2
(45) Date of Patent: Mar. 1, 2011

(54) SUBSTITUTED 1,8-NAPHTHYRIDINECARBOXAMIDES FOR USE AS PROLYL HYDROXYLASE INHIBITORS

(75) Inventors: Duke M. Fitch, Collegeville, PA (US); Mariela Colón, Collegeville, PA (US)

(73) Assignee: Glaxosmithkline, LLC, Philadelphia, PA (US)

( * ) Notice: Subject to any disclaimer, the term of this patent is extended or adjusted under 35 U.S.C. 154(b) by 0 days.

(21) Appl. No.: 12/281,677

(22) PCT Filed: Mar. 6, 2007

(86) PCT No.: PCT/US2007/063359

§ 371 (c)(1), (2), (4) Date: Sep. 4, 2008

(87) PCT Pub. No.: WO2007/103905

PCT Pub. Date: Sep. 13, 2007

(65) Prior Publication Data

US 2009/0082357 A1    Mar. 26, 2009

Related U.S. Application Data

(60) Provisional application No. 60/779,737, filed on Mar. 7, 2006.

(51) Int. Cl.
*A61K 31/44* (2006.01)
(52) U.S. Cl. ........................... 514/300; 546/123
(58) Field of Classification Search .................. 514/300; 546/123
See application file for complete search history.

(56) References Cited

PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Hsieh, et al. Chronic intermittent administration of HIF prolyl hydroxylase inhibitor significantly induces erythropoietin and increases total hemoglobin in normal rhesus macaques. Blood, Nov. 16, 2005, vol. 106, No. 11, Part 1, abstract p. 169A, see entire abstract.

* cited by examiner

*Primary Examiner* — James O Wilson
*Assistant Examiner* — Douglas M Willis
(74) *Attorney, Agent, or Firm* — Tony W. Peng; Edward R. Gimmi; Charles M. Kinzig

(57) ABSTRACT

The invention described herein relates to certain bicyclic heteroaromatic N-substituted glycine derivatives of formula (I)

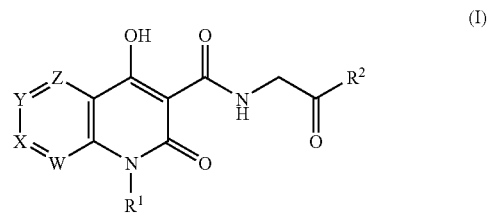

which are antagonists of HIF prolyl hydroxylases and are useful for treating diseases benefiting from the inhibition of this enzyme, anemia being one example.

2 Claims, No Drawings

SUBSTITUTED 1,8-NAPHTHYRIDINECARBOXAMIDES FOR USE AS PROLYL HYDROXYLASE INHIBITORS

CROSS REFERENCE TO PRIOR APPLICATION

This application is a 35 U.S.C. 371 application, which claims the benefit of U.S. Provisional Application No. 60/779,737 filed 7 Mar. 2006.

FIELD OF THE INVENTION

This invention relates to certain bicyclic heteroaromatic N-substituted glycine derivatives that are inhibitors of HIF prolyl hydroxylases, and thus have use in treating diseases benefiting from the inhibition of this enzyme, anemia being one example.

BACKGROUND OF THE INVENTION

Anemia occurs when there is a decrease or abnormality in red blood cells, which leads to reduced oxygen levels in the blood. Anemia occurs often in cancer patients, particularly those receiving chemotherapy. Anemia is often seen in the elderly population, patients with renal disease, and in a wide variety of conditions associated with chronic disease.

Frequently, the cause of anemia is reduced erythropoietin (Epo) production resulting in prevention of erythropoiesis (maturation of red blood cells). Epo production can be increased by inhibition of prolyl hydroxylases that regulate hypoxia inducible factor (HIF).

One strategy to increase erythropoietin (Epo) production is to stabilize and thus increase the transcriptional activity of the HIF. HIF-alpha subunits (HIF-1alpha, HIF-2alpha, and HIF-3alpha) are rapidly degraded by proteosome under normoxic conditions upon hydroxylation of proline residues by prolyl hydroxylases (EGLN 1, 2, 3). Proline hydroxylation allows interaction with the von Hippel Lindau (VHL) protein, a component of an E3 ubiquitin ligase. This leads to ubiquitination of HIF-alpha and subsequent degradation. Under hypoxic conditions, the inhibitory activity of the prolyl hydroxylases is suppressed, HIF-alpha subunits are therefore stabilized, and HIF-responsive genes, including Epo, are transcribed. Thus, inhibition of prolyl hydroxylases results in increased levels of HIF-alpha and thus increased Epo production.

The compounds of this invention provide a means for inhibiting these hydroxylases, increasing Epo production, and thereby treating anemia. Ischemia, stroke, and cytoprotection may also benefit by administering these compounds.

SUMMARY OF THE INVENTION

In the first instance, this invention relates to a compound of formula (I):

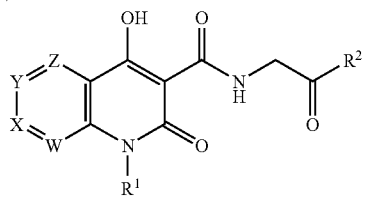

(I)

wherein:

$R^1$ is hydrogen, —$NR^3R^4$, —$C_1$-$C_{10}$alkyl, —$C_2$-$C_{10}$alkenyl, —$C_2$-$C_{10}$alkynyl, —$C_3$-$C_8$cycloalkyl, —$C_1$-$C_{10}$alkyl-$C_3$-$C_8$cycloalkyl, —$C_5$-$C_8$cycloalkenyl, —$C_1$-$C_{10}$alkyl-$C_5$-$C_8$cycloalkenyl, —$C_3$-$C_8$ heterocycloalkyl, —$C_1$-$C_{10}$alkyl-$C_3$-$C_8$ heterocycloalkyl, -aryl, —$C_1$-$C_{10}$alkyl-aryl, -heteroaryl or —$C_1$-$C_{10}$alkyl-heteroaryl;

$R^2$ is —$NR^6R^7$ or —$OR^8$;

$R^3$ and $R^4$ are each independently selected from the group consisting of hydrogen, —$C_1$-$C_{10}$ alkyl, —$C_3$-$C_8$cycloalkyl, —$C_1$-$C_{10}$ alkyl-$C_3$-$C_8$cycloalkyl, —$C_3$-$C_8$heterocycloalkyl, —$C_1$-$C_{10}$alkyl-$C_3$-$C_8$heterocycloalkyl, -aryl, —$C_1$-$C_{10}$alkyl-aryl, -heteroaryl, —$C_1$-$C_{10}$alkyl-heteroaryl, —CO($C_1$-$C_4$ alkyl), —CO($C_3$-$C_6$ cycloalkyl), —CO($C_3$-$C_6$ heterocycloalkyl), —CO(aryl), —CO(heteroaryl), —$SO_2$($C_1$-$C_4$ alkyl); or $R^3$ and $R^4$ taken together with the nitrogen to which they are attached form a 5- or 6- or 7-membered saturated ring optionally containing one other heteroatom selected from oxygen, nitrogen and sulphur;

$R^6$ and $R^7$ are each independently selected from the group consisting of hydrogen, —$C_1$-$C_{10}$ alkyl, —$C_2$-$C_{10}$ alkenyl, —$C_2$-$C_{10}$ alkynyl, —$C_3$-$C_8$ cycloalkyl, —$C_3$-$C_8$ heterocycloalkyl, -aryl and -heteroaryl;

$R^8$ is H or a cation, or —$C_1$-$C_{10}$alkyl which is unsubstituted or substituted with one or more substituents independently selected from the group consisting of —$C_3$-$C_6$ cycloalkyl, -heterocycloalkyl, -aryl, and -heteroaryl;

W, X, Y, and Z are independently $CR^9$ or nitrogen and at least 1 or 2 of W, X, Y, or Z is nitrogen but not all are nitrogen simultaneously;

each $R^9$ is independently selected from the group consisting of hydrogen, nitro, cyano, halogen, mono-, di- or trihalo substituted —$C_1$-$C_4$ alkyl, —C(O)$R^5$, —C(O)O$R^5$, —O$R^5$, —S$R^5$, —S(O)$R^5$, —S(O)$_2R^5$, —$NR^3R^4$, —CON$R^3R^4$, —N($R^3$)C(O)$R^5$, —N($R^3$)C(O)O$R^5$, —N($R^3$)$CH_2$C(O)O$R^5$, —OC(O)$NR^3R^4$, —N($R^3$)C(O)$NR^3R^4$, —P(O)(O$R^5$)$_2$, —$SO_2NR^3R^4$, —N($R^3$)SO$_2R^5$ and a —$C_1$-$C_{10}$ alkyl, —$C_1$-$C_{10}$ alkenyl, —$C_1$-$C_{10}$ alkynyl, —$C_3$-$C_6$ cycloalkyl, —$C_3$-$C_6$ heterocycloalkyl, -aryl and -heteroaryl group;

each $R^5$ is independently selected from the group consisting of hydrogen, —$C_1$-$C_{10}$alkyl, —$C_2$-$C_{10}$alkenyl, —$C_2$-$C_{10}$alkynyl, —CO($C_1$-$C_4$ alkyl), —CO(aryl), —CO(heteroaryl), —CO($C_3$-$C_6$ cycloalkyl), —CO($C_3$-$C_6$ heterocycloalkyl), —$SO_2$($C_1$-$C_4$ alkyl), —$C_3$-$C_8$ cycloalkyl, —$C_3$-$C_8$heterocycloalkyl, —$C_6$-$C_{14}$ aryl, —$C_1$-$C_{10}$alkyl-aryl, -heteroaryl, and —$C_1$-$C_{10}$alkyl-heteroaryl;

where any carbon or heteroatom of $R^1$, $R^2$, $R^3$, $R^4$, $R^5$, $R^6$, $R^7$, $R^8$ or $R^9$ is unsubstituted or, where possible, is substituted with one or more substituents independently selected from the group consisting of —$C_1$-$C_6$ alkyl; mono-, di- or trihalo substituted —$C_1$-$C_4$ alkyl; -aryl; -heteroaryl; halogen; —O$R^5$; —$NR^3R^4$; cyano; nitro; —C(O)$R^5$; —C(O)O$R^5$; —S$R^5$; —S(O)$R^5$; —S(O)$_2R^5$; —$NR^3R^4$; —CON$R^3R^4$; —N($R^3$)C(O)$R^5$; —N($R^3$)C(O)O$R^5$; —OC(O)$NR^3R^4$; —N($R^3$)C(O)$NR^3R^4$; —$SO_2NR^3R^4$; —N($R^3$)SO$_2R^5$; —$C_1$-$C_{10}$ alkenyl; —$C_1$-$C_{10}$ alkynyl; —$C_3$-$C_6$ cycloalkyl; —$C_3$-$C_6$ heterocycloalkyl; -aryl and -heteroaryl group; wherein $R^3$, $R^4$, and $R^5$ are the same as defined above;

or a pharmaceutically acceptable salt thereof.

In a second aspect of the present invention, there is provided a compound of formula (I) or a salt or solvate thereof for use in mammalian therapy, e.g. treating amenia. An example of this therapeutic approach is that of a method for treating anemia caused by increasing the production of erythropoietin (Epo) by inhibiting HIF prolyl hydroxylases comprising administering a compound of formula (I) to a patient in need thereof, neat or admixed with a pharmaceutically acceptable excipient, in an amount sufficient to increase production of Epo.

In a third aspect of the present invention, there is provided a pharmaceutical composition comprising a compound of formula (I) or a salt, solvate, or the like thereof, and one or more of pharmaceutically acceptable carriers, diluents and excipients.

In a fourth aspect, there is provided the use of a compound of formula (I) or a salt or solvate thereof in the preparation of a medicament for use in the treatment of a disorder mediated by inhibiting HIF prolyl hydroxylases, such as an anemia, that can be treated by inhibiting HIF prolyl hydroxylases.

DETAILED DESCRIPTION OF THE INVENTION

For the avoidance of doubt, unless otherwise indicated, the term "substituted" means substituted by one or more defined groups. In the case where groups may be selected from a number of alternative groups the selected groups may be the same or different.

The term "independently" means that where more than one substituent is selected from a number of possible substituents, those substituents may be the same or different.

An "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein the term "alkyl" refers to a straight- or branched-chain hydrocarbon radical having the specified number of carbon atoms, so for example, as used herein, the terms "$C_1$-$C_4$ alkyl", "$C_1$-$C_4$ alkyl" and "$C_1$-$C_{10}$ alkyl" refers to an alkyl group having at least 1 and up to 4, 6 or 10 carbon atoms respectively. Examples of such branched or straight-chained alkyl groups useful in the present invention include, but are not limited to, methyl, ethyl, n-propyl, isopropyl, isobutyl, n-butyl, t-butyl (1,1-dimethylethyl), n-pentyl, isopentyl (3-methylbutyl), 3,3-dimethylbutyl, n-hexyl, n-heptyl, n-octyl, n-nonyl, and n-decyl, and branched analogs of the latter 5 normal alkanes.

When the term "alkenyl" (or "alkenylene") is used it refers to straight or branched hydrocarbon chains containing the specified number of carbon atoms and at least 1 and up to 5 carbon-carbon double bonds. Examples include ethenyl (or ethenylene) and propenyl (or propenylene).

When the term "alkynyl" (or "alkynylene") is used it refers to straight or branched hydrocarbon chains containing the specified number of carbon atoms and at least 1 and up to 5 carbon-carbon triple bonds. Examples include ethynyl (or ethynylene) and propynyl (or propynylene).

When "cycloalkyl" is used it refers to a non-aromatic, saturated, cyclic hydrocarbon ring containing the specified number of carbon atoms. So, for example, the term "$C_3$-$C_8$ cycloalkyl" or "$C_3$-$C_6$cycloalkyl" refers to a non-aromatic cyclic hydrocarbon ring having from three to eight carbon atoms. Exemplary "$C_3$-$C_8$ cycloalkyl" and "$C_3$-$C_6$cycloalkyl" groups useful in the present invention include, but are not limited to, cyclopropyl, cyclobutyl, cyclopentyl, cyclohexyl, cycloheptyl and cyclooctyl.

The term "$C_5$-$C_8$cycloalkenyl" refers to a non-aromatic monocyclic carboxycyclic ring having the specified number of carbon atoms and up to 3 carbon-carbon double bonds. "Cycloalkenyl" includes by way of example cyclopentenyl and cyclohexenyl.

Where "$C_3$-$C_8$ heterocycloalkyl" is used, it means a non-aromatic heterocyclic ring containing the specified number of ring atoms being, saturated or having one or more degrees of unsaturation and containing one or more heteroatom substitutions selected from O, S and/or N. Such a ring may be optionally fused to one or more other "heterocyclic" ring(s) or cycloalkyl ring(s). Examples of "heterocyclic" moieties include, but are not limited to, aziridine, thiirane, oxirane, azetidine, oxetane, thietane, tetrahydrofuran, pyran, 1,4-dioxane, 1,3-dioxane, piperidine, piperazine, 2,4-piperazinedione, pyrrolidine, imidazolidine, pyrazolidine, morpholine, thiomorpholine, tetrahydrothiopyran, tetrahydrothiophene, and the like.

"Aryl" refers to optionally substituted monocyclic and polycarbocyclic unfused or fused groups having 6 to 14 carbon atoms and having at least one aromatic ring that complies with Hüickel's Rule. Examples of aryl groups are phenyl, biphenyl, naphthyl, anthracenyl, phenanthrenyl and the like.

"Heteroaryl" means an optionally substituted aromatic monocyclic ring or polycarbocyclic fused ring system wherein at least one ring complies with Hüickel's Rule, has the specified number of ring atoms, and that ring contains at least one heteratom selected from N, O, and/or S. Examples of "heteroaryl" groups include furanyl, thiophenyl, pyrrolyl, imidazolyl, pyrazolyl, triazolyl, tetrazolyl, thiazolyl, oxazolyl, isoxazolyl, oxadiazolyl, oxo-pyridyl, thiadiazolyl, isothiazolyl, pyridinyl, pyridazinyl, pyrazinyl, pyrimidinyl, quinolinyl, isoquinolinyl, benzofuranyl, benzothiophenyl, indolyl, and indazolyl.

The term "optionally" means that the subsequently described event(s) may or may not occur, and includes both event(s), which occur, and events that do not occur.

The term "solvate" refers to a complex of variable stoichiometry formed by a solute and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water.

Herein, the term "pharmaceutically-acceptable salts" refers to salts that retain the desired biological activity of the subject compound and exhibit minimal undesired toxicological effects. These pharmaceutically-acceptable salts may be prepared in situ during the final isolation and purification of the compound, or by separately reacting the purified compound in its free acid or free base form with a suitable base or acid, respectively.

In certain embodiments, compounds according to Formula I may contain an acidic functional group, one acidic enough to form salts. Representative salts include pharmaceutically-acceptable metal salts such as sodium, potassium, lithium, calcium, magnesium, aluminum, and zinc salts; carbonates and bicarbonates of a pharmaceutically-acceptable metal cation such as sodium, potassium, lithium, calcium, magnesium, aluminum, and zinc; pharmaceutically-acceptable organic primary, secondary, and tertiary amines including aliphatic amines, aromatic amines, aliphatic diamines, and hydroxy alkylamines such as methylamine, ethylamine, 2-hydroxyethylamine, diethylamine, triethylamine, ethylenediamine, ethanolamine, diethanolamine, and cyclohexylamine.

In certain embodiments, compounds according to Formula (I) may contain a basic functional group and are therefore capable of forming pharmaceutically-acceptable acid addition salts by treatment with a suitable acid. Suitable acids include pharmaceutically-acceptable inorganic acids and pharmaceutically-acceptable organic acids. Representative pharmaceutically-acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), and napthalene-2-sulfonate.

Exemplary Compounds

Compounds of particular interest include those wherein:

W is nitrogen and X, Y and Z are $CR^9$; X is nitrogen and W, Y and Z are $CR^9$; W and Z are nitrogen and X and Y are $CR^9$; Y is nitrogen and W, X and Z are $CR^9$; W and Y are nitrogen and X and Z are $CR^9$; or Z is nitrogen and W, X and Y are $CR^9$.

$R^1$ is hydrogen, —$C_1$-$C_{10}$alkyl, —$C_1$-$C_{10}$alkyl-$NR^3R^4$, —$C_3$-$C_8$cycloalkyl, —$C_1$-$C_{10}$alkyl, —$C_3$-$C_8$cycloalkyl, —$C_3$-$C_8$-heterocycloalkyl, —$C_1$-$C_{10}$alkyl-$C_3$-$C_8$-heterocycloalkyl, —$C_1$-$C_{10}$alkyl-aryl, —$C_1$-$C_{10}$alkyl-aryl-$C_1$-$C_4$alkyl, or —$C_1$-$C_{10}$alkyl-aryl-halo;

$R^2$ is —$NR^6R^7$ or —$OR^8$;

$R^3$ and $R^4$ are each independently hydrogen or —$C_1$-$C_{10}$ alkyl;

$R^6$ and $R^7$ are each independently selected from the group consisting of hydrogen, —$C_1$-$C_{10}$ alkyl, —$C_2$-$C_{10}$ alkenyl, —$C_2$-$C_{10}$ alkynyl, —$C_3$-$C_8$ cycloalkyl, —$C_3$-$C_8$ heterocycloalkyl, aryl and heteroaryl;

$R^8$ is H, a cation, or $C_1$-$C_{10}$alkyl;

each $R^9$ is independently selected from the group consisting of hydrogen, halogen, trifluoromethyl, —$OR^5$, —$N(R^3)CH_2C(O)OR^5$, unsubstituted or substituted-phenyl or —$C_1$-$C_4$ alkylphenyl, and —$C_1$-$C_4$ alkyl;

each $R^5$ is hydrogen or —$C_1$-$C_4$alkyl.

Of further particular interest are those compounds wherein:

W is nitrogen and X, Y and Z are $CR^9$; X is nitrogen and W, Y and Z are $CR^9$; W and Z are nitrogen and X and Y are $CR^9$; Y is nitrogen and W, X and Z are $CR^9$; W and Y are nitrogen and X and Z are $CR^9$; or Z is nitrogen and W, X and Y are $CR^9$.

$R^1$ is hydrogen, —$C_1$-$C_6$alkyl, —$C_1$-$C_4$alkyl-$NR^3R^4$, —$C_1$-$C_4$alkyl-$C_3$-$C_6$cycloalkyl, —$C_1$-$C_4$alkyl-phenyl, —$C_1$-$C_4$alkyl-phenyl-halo;

$R^2$ is —$OR^8$;

$R^3$ and $R^4$ are each independently hydrogen or —$C_1$-$C_4$alkyl;

each $R^5$ is independently hydrogen or $C_1$-$C_4$alkyl;

$R^8$ is H, a cation, or $C_1$-$C_{10}$alkyl;

each $R^9$ is independently selected from the group consisting of hydrogen, halogen, trifluoromethyl, —$N(R^3)CH_2C(O)OR^5$, —$OR^5$, unsubstituted or substituted phenyl or —$C_1$-$C_4$ alkylphenyl, and —$C_1$-$C_4$ alkyl.

All of the foregoing compounds of interest include their pharmaceutically acceptable salts, where applicable.

Specific examples of compounds of Formula (I) are found in the Examples set forth below.

Processes for preparing the compound of formula (I) are also within the ambit of this invention. To illustrate, process for preparing a compound of formula (I)

(I)

[Chemical structure showing a bicyclic system with OH, Y-Z-X-W ring, N-R¹, carbonyl, N-H, CH₂, C(O)R²]

wherein $R^1$, $R^2$, W, X, Y and Z are the same as defined above for formula (I), the process comprising:

1) treating a compound of formula A

A

[Chemical structure showing a fused pyridine-oxazinedione ring system with N-R1]

where R1 is the same as in formula (I) with a malonate diester, such as diethyl malonate, and a suitable base, such as 1,8-diazabicyclo[5.4.0]undec-7-ene, neat or in a suitable organic solvent, such as 1,4-dioxane, and heating the solution, either thermally or under microwave irradiation, followed by addition of glycine and further heating to provide a compound of formula (I) where $R^2$ is OH; or 2) treating a compound of formula B

B

[Chemical structure showing bicyclic system with OH, Y-Z-X-W ring, N-R1, carbonyl, OR']

wherein $R^1$, W, X, Y and Z are the same as for those groups in formula (I) and R' is a ester-forming group, with glycine sodium salt or glycine and an appropriate base, such as 1,8-diazabicyclo[5.4.0]undec-7-ene, sodium ethoxide or sodium hydride, in an appropriate solvent, such as ethanol or 1,4-dioxane, under either conventional thermal conditions or by microwave irradiation, to form a compound of formula (I) where $R^2$ is —OH.

The compounds of formula (I) may be prepared in crystalline or non-crystalline form, and, if crystalline, may optionally be solvated, e.g. as the hydrate. This invention includes within its scope stoichiometric solvates (e.g. hydrates) as well as compounds containing variable amounts of solvent (e.g. water).

Certain of the compounds described herein may contain one or more chiral atoms, or may otherwise be capable of existing as two enantiomers. The compounds claimed below include mixtures of enantiomers as well as purified enantiomers or enantiomerically enriched mixtures. Also included within the scope of the invention are the individual isomers of the compounds represented by formula (I), or claimed below, as well as any wholly or partially equilibrated mixtures thereof. The present invention also covers the individual isomers of the claimed compounds as mixtures with isomers thereof in which one or more chiral centers are inverted. Also, it is understood that any tautomers and mixtures of tautomers of the claimed compounds are included within the scope of the compounds of formula (I) as disclosed herein above or claimed herein below.

Where there are different isomeric forms they may be separated or resolved one from the other by conventional methods, or any given isomer may be obtained by conventional synthetic methods or by stereospecific or asymmetric syntheses.

While it is possible that, for use in therapy, a compound of formula (I), as well as salts, solvates and the like, may be administered as a neat preparation, i.e. no additional carrier, the more usual practice is to present the active ingredient confected with a carrier or diluent. Accordingly, the invention further provides pharmaceutical compositions, which includes a compound of formula (I) and salts, solvates and the like, and one or more pharmaceutically acceptable carriers, diluents, or excipients. The compounds of formula (I) and salts, solvates, etc, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula (I), or salts, solvates etc, with one or more pharmaceutically acceptable carriers, diluents or excipients.

It will be appreciated by those skilled in the art that certain protected derivatives of compounds of formula (I), which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". Further, certain compounds of the invention may act as prodrugs of other compounds of the invention. All protected derivatives and prodrugs of compounds of the invention are included within the scope of the invention. Examples of suitable pro-drugs for the compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosures in which documents are incorporated herein by reference). It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within compounds of the invention. Preferred prodrugs for compounds of the invention include: esters, carbonate esters, hemi-esters, phosphate esters, nitro esters, sulfate esters, sulfoxides, amides, carbamates, azo-compounds, phosphamides, glycosides, ethers, acetals and ketals.

Pharmaceutical compositions may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the formula (I), depending on the condition being treated, the route of administration and the age, weight and condition of the patient, or pharmaceutical compositions may be presented in unit dose forms containing a predetermined amount of active ingredient per unit dose. Preferred unit dosage compositions are those containing a daily dose or sub-dose, as herein above recited, or an appropriate fraction thereof, of an active ingredient. Furthermore, such pharmaceutical compositions may be prepared by any of the methods well known in the pharmacy art.

Pharmaceutical compositions may be adapted for administration by any appropriate route, for example by the oral (including buccal or sublingual), rectal, nasal, topical (including buccal, sublingual or trans dermal), vaginal or parenteral (including subcutaneous, intramuscular, intravenous or intradermal) route. Such compositions may be prepared by any method known in the art of pharmacy, for example by bringing into association a compound of formal (I) with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of a compound of formula (I). Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit pharmaceutical compositions for oral administration can be microencapsulated. The formulation can also be prepared to prolong or sustain the release as for example by coating or embedding particulate material in polymers, wax or the like.

Pharmaceutical compositions adapted for rectal administration may be presented as suppositories or as enemas.

Pharmaceutical compositions adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The pharmaceutical compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the pharmaceutical compositions may include other agents conventional in the art having regard to the type of formulation in question, for example those suitable for oral administration may include flavouring agents.

A therapeutically effective amount of a compound of the present invention will depend upon a number of factors including, for example, the age and weight of the intended recipient, the precise condition requiring treatment and its severity, the nature of the formulation, and the route of administration, and will ultimately be at the discretion of the attendant prescribing the medication. However, an effective amount of a compound of formula (I) for the treatment of anemia will generally be in the range of 0.1 to 100 mg/kg body weight of recipient per day and more usually in the range of 1 to 10 mg/kg body weight per day. Thus, for a 70 kg adult mammal, the actual amount per day would usually be from 70 to 700 mg and this amount may be given in a single dose per day or more usually in a number (such as two, three, four, five or six) of sub-doses per day such that the total daily dose is the same. An effective amount of a salt or solvate, etc., may be determined as a proportion of the effective amount of the compound of formula (I) per se. It is envisaged that similar dosages would be appropriate for treatment of the other conditions referred to above.

DEFINITIONS rt—room temperature
DMF—dimethylformamide
THF—tetrahydrofuran
DBU—1,8-diazabicyclo[5.4.0]undec-7-ene
TFA—Trifluoroacetic acid Chemical Background:

The compounds of this invention may be made by a variety of methods, including standard chemistry. Any previously defined variable will continue to have the previously defined meaning unless otherwise indicated. Illustrative general synthetic methods are set out below and then specific compounds of the invention as prepared are given in the examples.

Compounds of general formula (I) may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) *Protecting Groups in Organic Synthesis*, John Wiley & Sons). These groups are removed at a convenient stage of the compound synthesis using methods that are readily apparent to those skilled in the art. The selection of processes as well as the reaction conditions and order of their execution shall be consistent with the preparation of compounds of formula (I). Those skilled in the art will recognize if a stereocenter exists in compounds of formula (I). Accordingly, the present invention includes both possible stereoisomers and includes not only racemic compounds but the individual enantiomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, *Stereochemistry of Organic Compounds* by E. L. Eliel, S. H. Wilen, and L. N. Mander (Wiley-Interscience, 1994).

The compounds described herein may be made from commercially available starting materials or synthesized using known organic, inorganic and/or enzymatic processes. An illustrative method for making these starting compounds and intermediates can be found in a WIPO-published patent application, namely:

D. Chai, M. G. Darcy, D. Dhanak, K. J. Duffy, G. A. Erickson, D. M. Fitch, A. T. Gates, V. K. Johnston, R. T. Sarisky, M. J. Sharp, A. N. Shaw, R. Tedesco, K. J. Wiggall, M. N. Zimmerman "Quinolinylthiadiazine dioxides as antiviral agents for treating hepatitis C" PCT Int. Appl. (2002), WO 2002098424 A1

See also M. G. Darcy, D. Dhanak, K. J. Duffy, D. M. Fitch, R. T. Sarisky, A. N. Shaw, R. Tedesco, M. N. Zimmerman "Preparation of 1,1-dioxodihydrobenzothiadiazines as antiviral agents" PCT Int. Appl. (2003), WO 2003059356 A2.

Illustrated Methods of Preparation

Chemical Background:

M. G. Darcy, D. Dhanak, K. J. Duffy, D. M. Fitch, R. T. Sarisky, A. N. Shaw, R. Tedesco, M. N. Zimmerman "Preparation of 1,1-dioxodihydrobenzothiadiazines as antiviral agents" PCT Int. Appl. (2003), WO 2003059356 A2

Scheme I

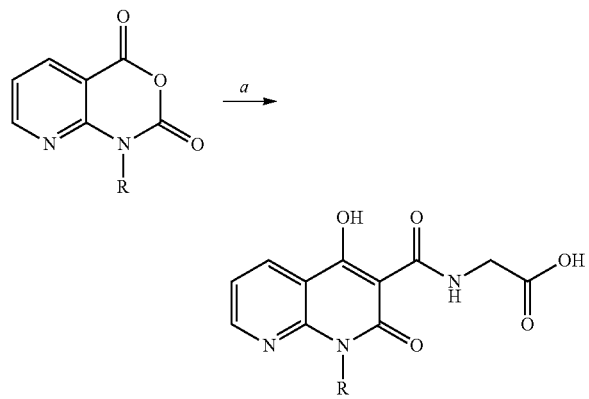

a) Diethyl malonate, DBU, 1,4-dioxane, 150° C., microwave then glycine, 200° C., microwave.

Scheme 2

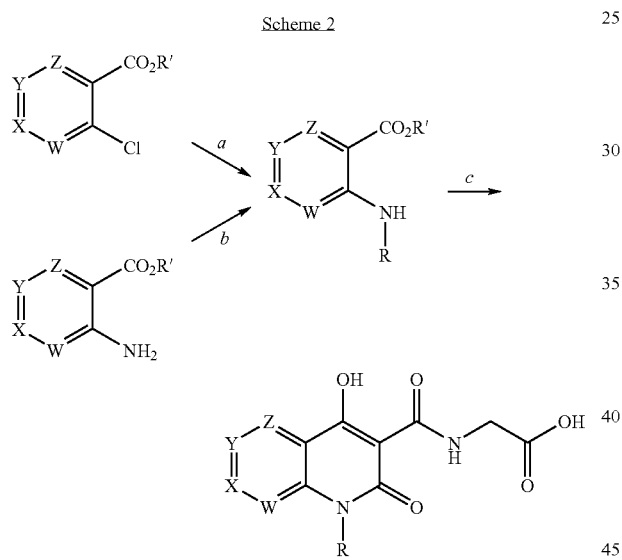

a) RNH₂, EtOH, microwave; b) NaCNBH₃, AcOH, CH₂Cl₂;
c) ClC(O)CH₂CO₂Et, Et₃N, CH₂Cl₂, then NaOEt, EtOH, then glycine, μwave or glycine, DBU, EtOH, microwave or glycine sodium salt, EtOH, microwave.

Scheme 3

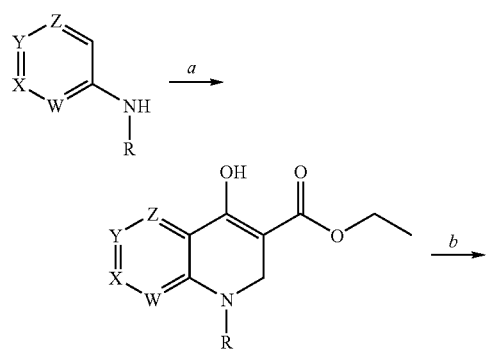

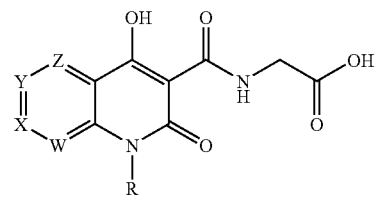

a) CH(CO₂Et)₃, 1,4-dioxane, microwave; b) glycine sodium salt, EtOH, microwave

Experimentals

Example 1

[Structure of N-{[1-(2-Cyclopropylethyl)-4-hydroxy-2-oxo-1,2-dihydro-1,8-naphthyridin-3-yl]carbonyl}glycine]

N-{[1-(2-Cyclopropylethyl)-4-hydroxy-2-oxo-1,2-dihydro-1,8-naphthyridin-3-yl]carbonyl}glycine A mixture of 1-(2-cyclopropylethyl)-2H-pyrido[2,3-d][1,3]oxazine-2,4 (1H)-dione (Prepared according to PCT Int. Appl. (2003), WO 2003059356 A2)(0.232 g, 1.00 mmol) and diethylmalonate (0.152 mL, 1.00 mmol) was treated with 1,8-diazabicyclo[5.4.0]undec-7-ene (0.300 mL, 2.00 mmol). 1,4-dioxane (1.0 mL) was added and the solution was heated to 150° C. for 20 min. in a Biotage Initiator microwave synthesizer (http://www.biotage.com). Following cooling, glycine (0.113 g, 1.50 mmol) was added and the solution was heated to 200° C. for 20 min. in a Biotage Initiator microwave synthesizer. The reaction mixture was then cooled, treated with 6M aqueous sodium hydroxide (2.0 mL), diluted with water and extracted with diethyl ether. The aqueous layer was then acidified with 6M aqueous hydrochloric acid and extracted twice with ethyl acetate. The organic solution was dried over MgSO₄, filtered, and concentrated in vacuo. The mixture was purified via preparative HPLC(YMC 75×30 mm column, 0.1% TFA in water and 0.1% TFA in acetonitrile) to afford the title compound as a white solid (0.008 g; 2.4%). ¹H NMR (400 MHz, DMSO-d₆) δ ppm 13.0 (s, 1H), 10.5 (t, J=5.6 Hz, 1H), 8.83 (dd, J=4.5, 1.8 Hz, 1H), 8.46 (dd, J=8.0, 1.9 Hz, 1H), 7.43 (dd, J=8.0, 4.7 Hz, 1H), 4.41-4.60 (m, 2H), 4.13 (d, J=5.6 Hz, 2H), 1.55 (q, J=7.3 Hz, 2H), 0.67-0.82 (m, 1H), 0.32-0.41 (m, 2H), −0.09-0.04 (m, 2H). MS(ES+) m/e 332 [M+H]$^+$.

Example 2

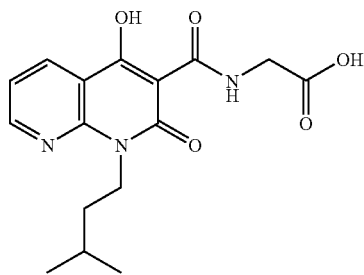

N-{[4-hydroxy-1-(3-methylbutyl)-2-oxo-1,2-dihydro-1,8-naphthyridin-3-yl]carbonyl}glycine 2a) Ethyl 2-[(3-methylbutyl)amino]-3-pyridinecarboxylate A mixture of ethyl-2-chloronicotinic carboxylate (2.00 g, 10.8 mmol) and 3-(methylbutyl)amine (1.88 mL, 16.1 mmol) in ethanol (3.0 mL) was heated to 180° C. for 40 min. in a Biotage Initiator microwave synthesizer. The mixture was added to a solution of saturated aqueous sodium bicarbonate and extracted twice with ethyl acetate. The combined organic portions were dried over magnesium sulfate, filtered, and concentrated in vacuo. The residue was purified via flash column chromatography (60% ethyl acetate in hexanes) to afford the title compound as a clear oil (2.05 g, 80%). $^1$H NMR (400 MHz, CHLOROFORM-d) δ ppm 8.30 (dd, J=4.7, 1.9 Hz, 1H), 8.13 (dd, J=7.6, 2.0 Hz, 1H), 7.94 (br. s., 1H), 6.51 (dd, J=7.8, 4.8 Hz, 1H), 4.33 (q, J=7.2 Hz, 2H), 3.48-3.58 (m, 2H), 1.68-1.82 (m, 1H), 1.51-1.63 (m, 2H), 1.39 (t, J=7.2 Hz, 3H), 0.97 (d, J=6.6 Hz, 6H). MS(ES+) m/e 237 [M+H]$^+$.

2b) ethyl 4-hydroxy-1-(3-methylbutyl)-2-oxo-1,2-dihydro-1,8-naphthyridine-3-carboxylate A solution of the compound from Example 2a) (2.05 g, 8.67 mmol) in methylene chloride (12.0 mL) was treated with ethyl malonyl chloride (1.31 mL, 10.4 mmol). The mixture was stirred for 1 h at ambient temperature and then treated with triethylamine (1.45 mL, 10.4 mmol) over 10 minutes until fuming ceased. The reaction mixture was stirred for 1.5 h at ambient temperature and then treated with another equivalent of ethyl malonyl chloride (1.09 mL, 8.67 mmol). The reaction mixture was stirred overnight at ambient temperature. Following concentration in vacuo, the residue was dissolved in ethanol (12 mL) and treated with sodium ethoxide (3.40 mL, 8.67 mmol, 21% solution in ethanol) and stirred for 2 h at ambient temperature. Additional sodium ethoxide (1.62 mL, 4.34 mmol, 21% solution in ethanol) was added and the reaction mixture stirred for 1 h. The reaction mixture was concentrated in vacuo and the residue was added to a solution of saturated aqueous sodium bicarbonate and extracted with ethyl acetate (3×10.0 mL). Acidification of the aqueous layer with 1 N aqueous hydrochloric acid, followed by extraction with ethyl acetate provided additional product. The organic portions were dried over magnesium sulfate, filtered, concentrated in vacuo, and purified via flash column chromatography (40% ethyl acetate in hexanes) to afford the title compound as a white powder (1.12 g, 42%). $^1$H NMR (400 MHz, DMSO-d$_6$) δ ppm 12.9 (br. s., 1H) 8.75 (dd, J=4.7, 1.9 Hz, 1H), 8.41 (dd, J=8.0, 1.9 Hz, 1H), 7.35 (dd, J=7.8, 4.5 Hz, 1H), 4.32 (q, J=7.0 Hz, 2H), 1.54-1.71 (m, 1H), 1.41-1.53 (m, 2H), 1.31 (t, J=7.1 Hz, 3H), 1.08-1.24 (m, 2H), 0.96 (s, 3H), 0.94 (s, 3H). MS(ES+) m/e 305 [M+H]$^+$.

2c) N-{[4-Hydroxy-1-(3-methylbutyl)-2-oxo-1,2-dihydro-1,8-naphthyridin-3-yl]carbonyl}glycine Glycine sodium salt (0.440 g, 4.53 mmol) was added to a solution of the compound from Example 2b) (0.690 g, 2.27 mmol) in 2-methoxyethanol (7.0 mL). The reaction mixture was heated to reflux for 2 h. The solution was then added to cold water, treated with 6N aqueous hydrochloric acid and the resulting precipitate was filtered and washed with water. The solid was swirled in ethyl ether and filtered to obtain a pale purple solid (0.464 g, 60%). $^1$H NMR (400 MHz, DMSO-d$_6$) δ ppm 13.0 (s, 1H), 10.5 (t, J=5.6 Hz, 1H), 8.85 (dd, J=4.7, 1.9 Hz, 1H), 8.47 (dd, J=7.8, 1.8 Hz, 1H), 7.44 (dd, J=8.0, 4.7 Hz, 1H), 4.40-4.48 (m, 2H), 4.14 (d, J=5.6 Hz, 2H), 1.61-1.74 (m, 1H), 1.48-1.60 (m, 2H), 0.97 (d, J=6.6 Hz, 6H). MS(ES+) m/e 334 [M+H]$^+$.

Example 3

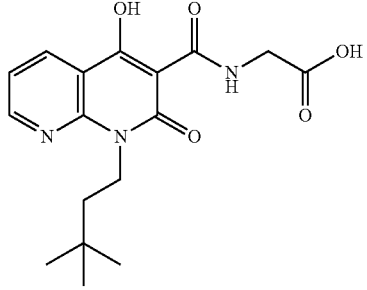

N-{[1-(3,3-dimethylbutyl)-4-hydroxy-2-oxo-1,2-dihydro-1,8-naphthyridin-3-yl]carbonyl}glycine 3a) Ethyl 2-[(3,3-dimethylbutyl)amino]-3-pyridinecarboxylate A mixture of ethyl-2-chloronicotinic carboxylate (0.518 g, 2.79 mmol) and (3,3-dimethylbutyl)amine (0.560 mL, 4.18 mmol) in ethanol (3.0 mL) was heated to 180° C. for 40 min. in a Biotage Initiator microwave synthesizer. The mixture was concentrated and the residue was diluted in water, treated with saturated aqueous sodium bicarbonate, and extracted with ethyl acetate. The combined organic portions were dried over magnesium sulfate, filtered, and concentrated in vacuo. The residue was purified via flash column chromatography (60% ethyl acetate in hexanes) to afford the title compound as a clear oil (0.655 g, 94%). $^1$H NMR (400 MHz, CHLOROFORM-d) δ ppm 8.31 (dd, J=4.8, 2.0 Hz, 1H), 8.12 (dd, J=7.6, 2.0 Hz, 1H), 7.87 (br. s., 1H), 6.51 (dd, J=7.6, 4.8 Hz, 1H), 4.33 (q, J=7.2 Hz, 2H), 3.30-3.61 (m, 2H), 1.55-1.68 (m, 2H), 1.39 (t, J=7.1 Hz, 3H), 1.00 (s, 9H). MS(ES+) m/e 251 [M+H]$^+$.

3b) ethyl 2-{(3,3-dimethylbutyl)[3-(ethyloxy)-3-oxopropanoyl]amino}-3-pyridinecarboxylate A solution of the compound from Example 3a) (0.650 g, 2.62 mmol) in methylene chloride (20.0 mL) was treated with triethylamine (0.500 mL, 3.63 mmol) and ethyl malonyl chloride (0.460 mL, 3.63 mmol). The mixture was stirred at ambient temperature for 2 h and then treated with additional ethyl malonyl chloride (0.460 mL, 3.63 mmol). The reaction mixture was stirred overnight at ambient temperature, and then treated with additional ethyl malonyl chloride (0.460 mL, 3.63 mmol) and triethylamine (0.500 mL, 3.63 mmol) and heated to 40° C. The mixture was cooled and filtered. The filtrate was purified via flash column chromatography (60% ethyl acetate in hexanes) to afford the title compound as a yellow oil (0.296 g, 30%). $^1$H NMR (400 MHz, CHLOROFORM-d) δ ppm 8.71 (dd, J=4.7, 1.9 Hz, 1H), 8.36 (dd, J=7.8, 1.9 Hz, 1H), 7.46 (dd, J=7.8, 4.8 Hz, 1H), 4.40 (d, J=7.1 Hz, 2H), 4.17-4.29 (m, 2H), 4.12 (q, J=7.2 Hz, 2H), 3.11 (s, 2H) 1.42-1.53 (m, 2H), 1.40 (t, J=7.1 Hz, 3H), 1.23 (t, J=6.6 Hz, 3H), 0.86 (s, 9H). MS(ES+) m/e 365 [M+H]$^+$.

3c) N-{[1-(3,3-dimethylbutyl)-4-hydroxy-2-oxo-1,2-dihydro-1,8-naphthyridin-3-yl]carbonyl}glycine A solution of the compound from Example 3b) (0.296 g, 0.81 mmol) in ethanol was treated with sodium ethoxide (0.390 mL, 1.00 mmol, 21% solution in ethanol) and stirred for 2 h at ambient temperature. Glycine (0.075 g, 1.00 mmol) was added and the solution was heated to 180° C. for 30 min. in a Biotage Initiator microwave synthesizer. The reaction mixture was filtered and the solid was stirred with 1 N aqueous hydrochloric acid for 2 h. The resulting precipitate was filtered and dried in vacuo to afford the title compound as a light brown powder (0.130 g, 46%). $^1$H NMR (400 MHz, DMSO-d$_6$) δ ppm 13.0 (s, 1H), 10.5 (t, J=4.7 Hz, 1H), 8.83 (dd, J=4.7, 1.9 Hz, 1H), 8.46 (dd, J=8.0, 1.9 Hz, 1H), 7.42 (dd, J=8.0, 4.7 Hz, 1H), 4.37-4.53 (m, 2H), 4.06 (d, J=5.3 Hz, 2H), 1.44-1.57 (m, 2H), 1.02 (s, 9H). MS(ES+) m/e 348 [M+H]$^+$.

Example 4

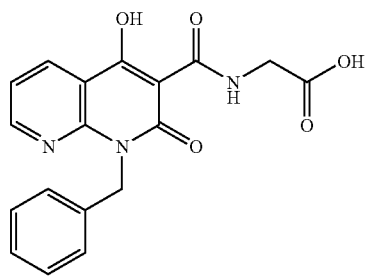

N-{[4-hydroxy-2-oxo-1-(phenylmethyl)-1,2-dihydro-1,8-naphthyridin-3-yl]carbonyl}glycine

4a) Ethyl 2-[(phenylmethyl)amino]-3-pyridinecarboxylate

A mixture of ethyl-2-chloronicotinic carboxylate (0.500 g, 2.70 mmol) and benzylamine (0.290 mL, 2.70 mmol) in ethanol (3.0 mL) was heated to 180° C. for 30 min. in a Biotage Initiator microwave synthesizer. Additional benzylamine (0.290 mL, 2.70 mmol) was added and the solution was heated to 180° C. for 30 min. in a Biotage Initiator microwave synthesizer. The mixture was added to water and extracted twice with ethyl acetate. The combined organic portions were dried over magnesium sulfate, filtered, and concentrated in vacuo. The residue was purified via flash column chromatography (60% ethyl acetate in hexanes) to afford the title compound as a yellow oil (0.480 g, 69%). $^1$H NMR (400 MHz, CHLOROFORM-d) δ ppm 8.27-8.41 (m, 2H), 8.18 (d, J=7.6 Hz, 1H), 7.21-7.45 (m, 5H), 6.58 (dd, J=7.7, 4.9 Hz, 1H), 4.79 (d, J=5.3 Hz, 2H), 4.34 (q, J=7.1 Hz, 2H), 1.39 (t, J=7.1 Hz, 3H). MS(ES+) m/e 257 [M+H]$^+$.

4b) N-{[4-Hydroxy-2-oxo-1-(phenylmethyl)-1,2-dihydro-1,8-naphthyridin-3-yl]carbonyl}glycine A solution of the compound from Example 4a) (0.480 g, 1.89 mmol) in dichloromethane (20.0 mL) was treated with triethylamine (0.410 mL, 2.97 mmol) followed by ethyl malonyl chloride (0.370 mL, 2.97 mmol). The mixture was stirred at ambient temperature for 1.5 h, followed by addition of water, and extraction twice with dichloromethane. The combined organic portions were dried over magnesium sulfate, filtered, and concentrated in vacuo. The residue was dissolved in ethanol (2.0 mL) and treated with sodium ethoxide (0.880 mL, 2.27 mmol, 21% solution in ethanol) at ambient temperature and stirred for 3 h. The solution was concentrated in vacuo and treated with water and 1N aqueous hydrochloric acid. The resulting solid was filtered, washed with water, and dried in vacuo. A solution of this solid (0.533 g, 1.60 mmol), 1,8-diazabicyclo[5.4.0]undec-7-ene (0.25 mL, 1.60 mmol) and glycine (0.12 g, 1.60 mmol) in ethanol (3.0 mL) was heated to 180° C. for 30 min. in a Biotage Initiator microwave synthesizer. The solution was concentrated in vacuo and purified via preparative HPLC(YMC 75×30 mm column, 0.1% TFA in water and 0.1% TFA in acetonitrile) to afford the title compound as a light orange solid (0.113 g, 20%). $^1$H NMR (400 MHz, METHANOL-d$_4$) δ ppm 13.0 (br. S., 1H), 10.5 (t, J=5.6 Hz, 1H), 8.80 (dd, J=4.5, 1.8 Hz, 1H), 8.57 (dd, J=7.8, 1.8 Hz, 1H), 7.44 (dd, J=8.0, 4.7 Hz, 1H), 7.17-7.41 (m, 5H), 5.77 (s, 2H), 4.24 (d, J=5.3 Hz, 2H). MS(ES+) m/e 354 [M+H]$^+$.

Example 5

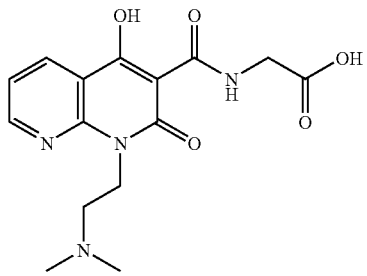

N-({1-[2-(dimethylamino)ethyl]-4-hydroxy-2-oxo-1,2-dihydro-1,8-naphthyridin-3-yl}carbonyl)glycine

5a) Ethyl 2-{[2-(dimethylamino)ethyl]amino}-3-pyridinecarboxylate

Following the procedure of Example 3a), except substituting N,N-dimethylethylenediamine for (3,3-dimethylbutyl)

amine, the title compound was obtained as an orange oil. $^1$H NMR (400 MHz, CHLOROFORM-d) δ ppm 8.28 (dd, J=4.7, 1.9 Hz, 1H), 8.13 (dd, J=7.6, 2.0 Hz, 1H), 6.51 (dd, J=7.8, 4.8 Hz, 1H), 4.34 (q, J=7.2 Hz, 2H), 3.58-3.64 (m, 2H), 2.58 (t, J=6.3 Hz, 2H), 2.31 (s, 6H), 1.39 (t, J=7.2 Hz, 3H). MS(ES+) m/e 238 [M+H]$^+$.

5b) N-({1-[2-(Dimethylamino)ethyl]-4-hydroxy-2-oxo-1,2-dihydro-1,8-naphthyridin-3-yl}carbonyl)glycine Following the procedure of Example 4b), except substituting the compound from Example 5a) for the compound from Example 4a), the title compound was obtained as a light pink solid. $^1$H NMR (400 MHz, DMSO-d$_6$) δ ppm 13.0 (br. s., 1H), 10.3 (t, J=5.6 Hz, 1H), 9.74 (br. s., 1H), 8.84 (dd, J=4.5, 1.8 Hz, 1H), 8.52 (dd, J=7.8, 1.8 Hz, 1H), 7.50 (dd, J=7.8, 4.8 Hz, 1H), 4.75 (t, J=6.1 Hz, 2H), 4.17 (d, J=5.6 Hz, 2H), 3.47 (t, J=5.9 Hz, 2H), 2.91 (s, 6H). MS(ES+) m/e 335[M+H]$^+$.

Example 6

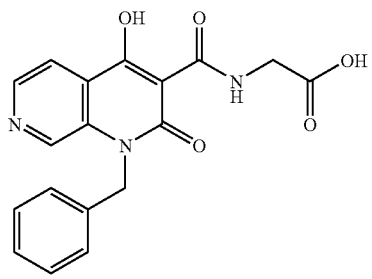

N-{[4-hydroxy-2-oxo-1-(phenylmethyl)-1,2-dihydro-1,7-naphthyridin-3-yl]carbonyl}glycine 6a) Ethyl 3-[(phenylmethyl)amino]-4-pyridinecarboxylate To a suspension of 3-aminoisonicotinic acid (0.600 g, 4.35 mmol) in ethanol (20 mL) was added concentrated sulfuric acid (0.40 mL) at ambient temperature. The solution was then refluxed overnight, cooled to ambient temperature, and neutralized to pH ~7 using 6N aqueous sodium hydroxide. The mixture was extracted with (3×20 mL) ethyl acetate. The combined organic portions were dried over magnesium sulfate, filtered, and concentrated in vacuo. The residue was dissolved in methanol (20 mL) and treated with benzaldehyde (0.440 mL, 4.35 mmol). The solution was stirred at ambient temperature for 1 h and then treated with portionwise addition of sodium cyanoborohydride (0.920 g, 4.35 mmol) followed by acetic acid (0.20 mL). The resulting mixture was stirred at ambient temperature for 1 h and then concentrated in vacuo. The residue was treated with 5% aqueous sodium hydrogen carbonate and extracted with ethyl acetate (3×20 mL). The combined organic portions were dried over magnesium sulfate, filtered, and concentrated in vacuo. The residue was purified via flash column chromatography (10% methanol in dichloromethane) to afford the desired product as a yellow oil (0.500 g, 45%). $^1$H NMR (400 MHz, CHLOROFORM-d) δ ppm 8.08 (s, 1H), 7.84 (d, J=5.3 Hz, 1H), 7.69 (d, J=4.5 Hz, 1H), 7.29-7.34 (m, 5H), 4.48 (d, J=5.6 Hz, 2H), 4.14 (q, J=7.2 Hz, 2H), 1.28 (t, J=7.2 Hz, 3H). MS(ES+) m/e 257 [M+H]$^+$.

6b) N-{[4-hydroxy-2-oxo-1-(phenylmethyl)-1,2-dihydro-1,7-naphthyridin-3-yl]carbonyl}glycine A solution of the compound from Example 6a) (0.500 g, 1.90 mmol) in methylene chloride (20.0 mL) was treated with (4-dimethylamino)pyridine (0.040 mL, 0.38 mmol) followed by ethyl malonyl chloride (0.260 mL, 2.09 mmol). The mixture was stirred overnight at ambient temperature, followed by addition of triethylamine (1.00 mL, 7.17 mmol). Following stirring 1 h at ambient temperature, the reaction mixture was concentration in vacuo. The residue was dissolved in ethanol (2.0 mL), treated with sodium ethoxide (0.700 mL, 1.90 mmol, 21% solution in ethanol) at ambient temperature, and stirred overnight. The solution was concentrated in vacuo, filtered through a plug of silica with ethyl acetate, and concentrated in vacuo. The resulting residue was dissolved in ethanol (3.0 mL) and treated with glycine sodium salt (0.110 g, 1.54 mmol) and 1,8-diazabicyclo[5.4.0]undec-7-ene (0.230 mL, 1.54 mmol) and heated to 180° C. for 30 min. in a Biotage Initiator microwave synthesizer. The reaction was diluted with water, acidified with 1 N aqueous hydrochloric acid, and the resulting precipitate was filtered, washed with methanol, and dried in vacuo to afford the title compound as a light brown solid (0.175 g, 32%). $^1$H NMR (400 MHz, METHANOL-d$_4$) δ ppm 13.0 (br. s., 1H), 10.5 (t, J=5.6 Hz, 1H), 8.75 (dd, J=4.7, 1.9 Hz, 1H), 8.54 (dd, J=8.0, 1.9 Hz, 1H), 7.31-7.43 (m, 3H), 7.14-7.30 (m, 3H), 5.75 (s, 2H), 4.20 (d, J=5.6 Hz, 2H). MS(ES+) m/e 354 [M+H]$^+$.

Example 7

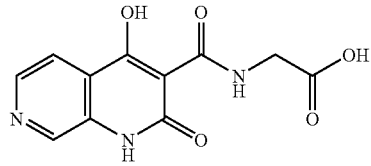

N-[(4-hydroxy-2-oxo-1,2-dihydro-1,7-naphthyridin-3-yl)carbonyl]glycine

A solution of ethyl 3-aminoisonicotinate (0.071 g, 0.43 mmol) in methylene chloride (2.0 mL) was treated with triethylamine (1.00 mL, 7.17 mmol) followed by ethyl malonyl chloride (0.060 mL, 0.47 mmol). The mixture was stirred overnight at ambient temperature, followed by concentration in vacuo. The residue was dissolved in ethanol (2.0 mL), treated with sodium ethoxide (0.158 mL, 0.43 mmol, 21% solution in ethanol) at ambient temperature, and stirred overnight. The solution was concentrated in vacuo, and the resulting residue was dissolved in ethanol (2.0 mL) and treated with glycine sodium salt (0.030 g, 0.43 mmol) and 1,8-diazabicyclo[5.4.0]undec-7-ene (0.060 mL, 0.43 mmol) and heated to 180° C. for 30 min. in a Biotage Initiator microwave synthesizer. The reaction was diluted with water, acidified with 1 N aqueous hydrochloric acid, and the resulting precipitate was filtered, washed with water, and dried in vacuo to afford the title compound as a light brown solid (0.034 g, 30%). $^1$H NMR (400 MHz, DMSO-d$_6$ δ ppm 12.4 (s, 2H), 10.4 (s, 2H), 8.88 (s, 1H), 7.89 (s, 1H), 4.15 (d, J=5.6 Hz, 2H). MS(ES+) m/e 264 [M+H]$^+$.

Example 8

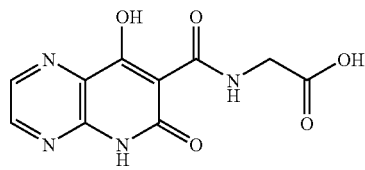

N-[(8-hydroxy-6-oxo-4,6-dihydropyrido[2,3-b]pyrazin-7-yl)carbonyl]glycine

Following the procedure of Example 7, except substituting methyl 3-amino-2-pyrazinecarboxylate for ethyl 3-aminoisonicotinate, the title compound was obtained as a brown solid. $^1$H NMR (400 MHz, DMSO-d$_6$ δ ppm 12.2 (s, 2H), 10.6 (t, J=5.3 Hz, 1H), 8.68 (d, J=2.3 Hz, 1H), 8.58 (d, J=2.0 Hz, 1H), 3.99 (d, J=5.3 Hz, 2H). MS(ES+) m/e 265 [M+H]$^+$.

Example 9

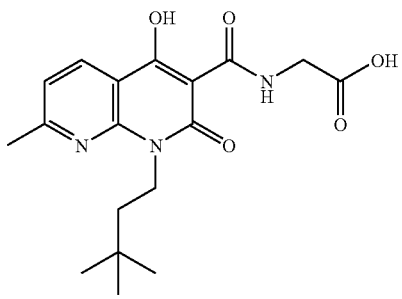

N-{[1-(3,3-dimethylbutyl)-4-hydroxy-7-methyl-2-oxo-1,2-dihydro-1,8-naphthyridin-3-yl]carbonyl}glycine 9a) Ethyl 2-[(3,3-dimethylbutyl)amino]-6-methyl-3-pyridinecarboxylate A solution of 2-chloro-6-methylnicotinic acid (0.500 g, 2.91 mmol) in ethanol (5.0 mL) was treated with potassium carbonate (0.810 g, 5.80 mmol) followed by (3,3-dimethylbutyl)amine (0.590 mL, 4.35 mmol). The mixture was stirred at reflux for 3 h and then heated to 160° C. for 1 h in a Biotage Initiator microwave synthesizer. A solid was decanted and the mother liquor was further diluted with ethanol (5.0 mL) and treated with concentrated sulfuric acid (3.0 mL). The solution was then refluxed overnight, cooled to ambient temperature, and neutralized to pH ~7 using 6N aqueous sodium hydroxide. The mixture was extracted with ethyl acetate (3×20 mL). The combined organic portions were dried over magnesium sulfate, filtered, and concentrated in vacuo. The title compound was obtained as a clear oil (0.578 g, 75%). $^1$H NMR (400 MHz, CHLOROFORM-d) δ ppm 7.99 (d, J=7.8 Hz, 1H), 7.84 (br. s., 1H), 6.35 (d, J=7.8 Hz, 1H), 4.30 (q, J=7.2 Hz, 2H), 3.44-3.58 (m, 2H), 2.92-3.05 (m, 2H), 2.42 (s, 3H), 1.37 (t, J=7.2 Hz, 3H), 0.99 (s, 9H). MS(ES+) m/e 265 [M+H]$^+$.

9b) Ethyl 1-(3,3-dimethylbutyl)-4-hydroxy-7-methyl-2-oxo-1,2-dihydro-1,8-naphthyridine-3-carboxylate A solution of the compound from Example 9a) (0.578 g, 2.18 mmol) in dichloromethane (20.0 mL) was treated with triethylamine (0.460 mL, 3.28 mmol) followed by ethyl malonyl chloride (0.410 mL, 3.28 mmol). The mixture was stirred overnight at ambient temperature, followed by concentration in vacuo. The residue was dissolved in ethanol (15.0 mL), treated with sodium ethoxide (1.70 mL, 4.36 mmol, 21% solution in ethanol) at ambient temperature, and stirred for 1 h. The solution was concentrated in vacuo and treated with water and 1N aqueous hydrochloric acid. The mixture was extracted with ethyl acetate (3×20 mL). The combined organic portions were dried over magnesium sulfate, filtered, and concentrated in vacuo. Purification via flash column chromatography (40-60% ethyl acetate in hexanes) afforded the title compound as a yellow-orange solid (0.371 g, 51%). $^1$H NMR (400 MHz, CHLOROFORM-d) δ ppm 14.0 (s, 1H), 8.12 (d, J=8.1 Hz, 1H), 6.91 (d, J=8.1 Hz, 1H), 4.36 (q, J=7.1 Hz, 2H), 3.25 (s, 3H), 1.40-1.49 (m, 2H), 1.36 (t, J=7.1 Hz, 3H), 0.93 (s, 9H). MS(ES+) m/e 333 [M+H]$^+$.

9c) N-{[1-(3,3-dimethylbutyl)-4-hydroxy-7-methyl-2-oxo-1,2-dihydro-1,8-naphthyridin-3-yl]carbonyl}glycine To a solution of the compound from Example 9b) (0.371 g, 1.11 mmol) in ethanol (2.0 mL) was added glycine sodium salt (0.217 g, 2.23 mmol). The mixture was heated to 150° C. for 15 min. in a Biotage Initiator microwave synthesizer. The reaction was quenched with 1 N aqueous hydrochloric acid and the resulting precipitate was filtered, washed with water, and dried in vacuo to afford the title compound as a light cream solid (0.066 g, 15%). $^1$H NMR (400 MHz, DMSO-d$_6$) δ ppm 12.9 (br. s., 1H), 10.5 (t, J=5.4 Hz, 1H), 8.32 (d, J=7.8 Hz, 1H), 7.30 (d, J=8.1 Hz, 1H), 4.37-4.50 (m, 2H), 4.12 (d, J=5.6 Hz, 2H), 2.62 (s, 3H), 1.47-1.57 (m, 2H), 1.02 (s, 9H). MS(ES+) m/e 362 [M+H]$^+$.

Example 10

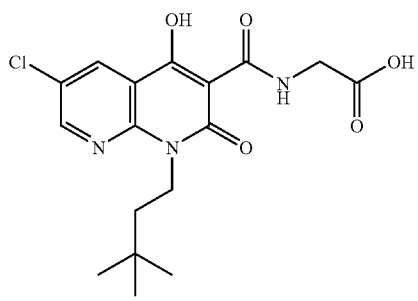

N-{[6-chloro-1-(3,3-dimethylbutyl)-4-hydroxy-2-oxo-1,2-dihydro-1,8-naphthyridin-3-yl]carbonyl}glycine 10a) Ethyl 5-chloro-2-[(3,3-dimethylbutyl)amino]-3-pyridinecarboxylate Following the procedure of Example 9a), except substituting methyl 2,5-dichloro-3-pyridinecarboxylate for 2-chloro-6-methylnicotinic acid, the title compound was obtained as a yellow solid following purification via flash column chromatography (30% ethyl acetate in hexanes). $^1$H NMR (400 MHz, CHLOROFORM-d) δ ppm 8.24 (d, J=2.8 Hz, 1H), 8.08 (d, J=2.5 Hz, 1H), 7.89 (s, 1H), 4.34 (q, J=7.1 Hz, 2H), 3.44-3.56 (m, 2H), 1.55-1.59 (m, 2H), 1.40 (t, J=7.1 Hz, 3H), 0.99 (s, 9H). MS(ES+) m/e 285 [M+H]$^+$.

10b) Ethyl 6-chloro-1-(3,3-dimethylbutyl)-4-hydroxy-2-oxo-1,2-dihydro-1,8-naphthyridine-3-carboxylate Following the procedure of Example 9b), except substituting the compound from Example 10a) for the compound from Example 9a), the title compound was obtained as a white solid. $^1$H NMR (400 MHz, METHANOL-d$_4$) δ ppm 8.64 (d, J=2.8 Hz, 1H), 8.29 (d, J=2.5 Hz, 1H), 4.48 (q, J=7.1 Hz, 2H), 4.25-4.40 (m, 2H), 1.50 (dd, J=8.0, 4.2 Hz, 2H), 1.45 (t, J=7.1 Hz, 3H), 1.04 (s, 9H). MS(ES+) m/e 353 [M+H]$^+$.

10c) N-{[6-chloro-1-(3,3-dimethylbutyl)-4-hydroxy-2-oxo-1,2-dihydro-1,8-naphthyridin-3-yl]carbonyl}glycine Following the procedure of Example 9c), except substituting the compound from Example 10b) for the compound from Example 9b), the title compound was obtained as a light pink solid. $^1$H NMR (400 MHz, DMSO-d$_6$) δ ppm 10.4 (t, J=6.1 Hz, 1H), 8.84 (d, J=2.8 Hz, 1H), 8.43 (d, J=2.5 Hz, 1H), 4.32-4.45 (m, 2H), 4.12 (d, J=5.6 Hz, 2H), 1.41-1.53 (m, 2H), 0.99 (s, 9H). MS(ES+) m/e 382 [M+H]$^+$.

Example 11

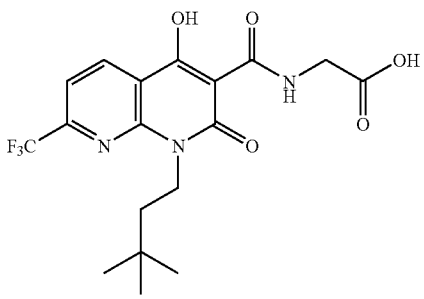

N-{[1-(3,3-dimethylbutyl)-4-hydroxy-2-oxo-7-(trifluoromethyl)-1,2-dihydro-1,8-naphthyridin-3-yl]carbonyl}glycine 11a) Ethyl 2-[(3,3-dimethylbutyl)amino]-6-(trifluoromethyl)-3-pyridinecarboxylate Following the procedure of Example 9a), except substituting 2-chloro-6-(trifluoromethyl)-3-pyridinecarboxylic acid for 2-chloro-6-methylnicotinic acid, the title compound was obtained as a yellow-orange solid. $^1$H NMR (400 MHz, METHANOL-d$_4$) δ ppm 8.28 (d, J=7.8 Hz, 1H), 8.14 (s, 1H), 6.87 (d, J=7.8 Hz, 1H), 4.35 (q, J=7.2 Hz, 2H), 3.49-3.60 (m, 2H), 1.50-161 (m, 2 H), 1.38 (t, J=7.2 Hz, 3H), 0.99 (s, 9H). MS(ES+) m/e 319 [M+H]$^+$.

11b) Ethyl 1-(3,3-dimethylbutyl)-4-hydroxy-2-oxo-7-(trifluoromethyl)-1,2-dihydro-1,8-naphthyridine-3-carboxylate Following the procedure of Example 9b), except substituting the compound from Example 11a) for the compound from Example 9a), the title compound was obtained as a clear yellow oil. $^1$H NMR (400 MHz, METHANOL-d$_4$) δ ppm 8.61 (d, J=7.8 Hz, 1H), 7.66 (d, J=8.1 Hz, 1H), 4.49 (q, J=7.1 Hz, 2H), 4.30-4.39 (m, 2H), 1.48-1.54 (m, 2H), 1.45 (t, J=7.1 Hz, 3H), 1.04 (s, 9H). MS(ES+) m/e 387 [M+H]$^+$.

11c) N-{[1-(3,3-dimethylbutyl)-4-hydroxy-2-oxo-7-(trifluoromethyl)-1,2-dihydro-1,8-naphthyridin-3-yl]carbonyl}glycine Following the procedure of Example 9c), except substituting the compound from Example 11b) for the compound from Example 9b), the title compound was obtained as a light cream solid. $^1$H NMR (400 MHz, DMSO-d$_6$) δ ppm 13.0 (br. s., 1H), 10.4 (t, J=5.1 Hz, 1H), 8.71 (d, J=8.1 Hz, 1H), 7.86 (d, J=8.1 Hz, 1H), 4.37-4.46 (m, 2H), 4.15 (d, J=5.8 Hz, 2H), 1.47-1.56 (m, 2H), 1.02 (s, 9H). MS(ES+) m/e 416 [M+H]$^+$.

Example 12

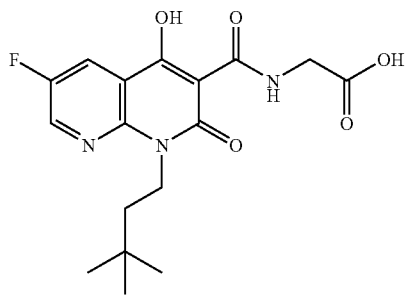

N-{[1-(3,3-dimethylbutyl)-6-fluoro-4-hydroxy-2-oxo-1,2-dihydro-1,8-naphthyridin-3-yl]carbonyl}glycine 12a) Ethyl 2-[(3,3-dimethylbutyl)amino]-5-fluoro-3-pyridinecarboxylate A solution of ethyl 2-chloro-5-fluoro-3-pyridinecarboxylate (0.300 g, 1.47 mmol) in ethanol (3.0 mL) was treated with (3,3-dimethylbutyl)amine (0.210 mL, 1.58 mmol). The mixture was heated to 150° C. for 0.5 h in a Biotage Initiator microwave synthesizer. The solution was diluted with ethyl acetate and washed with saturated aqueous sodium bicarbonate. The organic portion was dried over magnesium sulfate, filtered, and concentrated in vacuo. The title compound was obtained as an amber oil (0.347 g, 88%). $^1$H NMR (400 MHz, METHANOL-d$_4$) δ ppm 6.61 (d, J=3.0 Hz, 1H), 6.30 (dd, J=8.8, 3.0 Hz, 1H), 6.24 (br. s., 1H), 2.80 (q, J=7.1 Hz, 2H), 1.88-1.99 (m, 2H), −0.02-0.09 (m, 2H), −0.14 (t, J=7.2 Hz, 3H), −0.53 (s, 9H). MS(ES+) m/e 269 [M+H]⁺.

12b) Ethyl 1-(3,3-dimethylbutyl)-6-fluoro-4-hydroxy-2-oxo-1,2-dihydro-1,8-naphthyridine-3-carboxylate Following the procedure of Example 9b), except substituting the compound from Example 12a) for the compound from Example 9a), the title compound was obtained as a yellow orange oil. $^1$H NMR (400 MHz, METHANOL-$d_4$) δ ppm 8.64 (d, J=3.0 Hz, 1H), 8.08 (dd, J=7.8, 3.0 Hz, 1H), 4.47 (q, J=7.1 Hz, 2H), 4.32-4.38 (m, 2H), 1.50 (dd, J=7.8, 4.3 Hz, 2H), 1.45 (t, J=7.1 Hz, 3H), 1.03 (s, 9H). MS(ES+) m/e 337 [M+H]⁺.

12c) N-{[1-(3,3-dimethylbutyl)-6-fluoro-4-hydroxy-2-oxo-1,2-dihydro-1,8-naphthyridin-3-yl]carbonyl}glycine Following the procedure of Example 9c), except substituting the compound from Example 12b) for the compound from Example 9b), the title compound was obtained as a light orange solid. $^1$H NMR (400 MHz, DMSO-$d_6$) δ ppm 10.5 (t, J=5.3 Hz, 1H), 8.91 (d, J=3.0 Hz, 1H), 8.32 (dd, J=8.1, 3.0 Hz, 1H), 4.44 (dd, J=1.9, 4.8 Hz, 2H), 4.14 (d, J=5.8 Hz, 2H), 1.45-1.57 (m, 2H), 1.02 (s, 9H). MS(ES+) m/e 366 [M+H]⁺.

Example 13

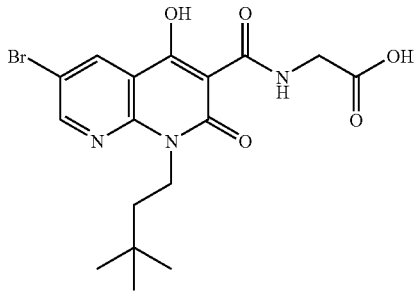

N-{[6-bromo-1-(3,3-dimethylbutyl)-4-hydroxy-2-oxo-1,2-dihydro-1,8-naphthyridin-3-yl]carbonyl}glycine 13a) Ethyl 5-bromo-2-[(3,3-dimethylbutyl)amino]-3-pyridinecarboxylate Following the procedure of Example 12a), except substituting methyl 5-bromo-2-chloro-3-pyridinecarboxylate for ethyl 2-chloro-5-fluoro-3-pyridinecarboxylate. A mixture of the title compound and the corresponding carboxylic acid was obtained. This mixture was dissolved in ethanol (3 mL), treated with concentrated sulfuric acid, and refluxed overnight. The solution was cooled to ambient temperature and neutralized with 6N sodium hydroxide, extracted with ethyl acetate, dried over magnesium sulfate, filtered, and concentrated in vacuo to give the title compound as an off-white solid (0.305 g, 78%). $^1$H NMR (400 MHz, METHANOL-$d_4$) δ ppm 8.27 (d, J=2.5 Hz, 1H), 8.19 (d, J=2.5 Hz, 1H), 4.35 (q, J=7.2 Hz, 2H), 3.45-3.56 (m, 2H), 2.85-2.99 (m, 2H), 1.39 (t, J=7.2 Hz, 3H), 1.00 (s, 9H). MS(ES+) m/e 331 [M+H]⁺.

13b) Ethyl 6-bromo-1-(3,3-dimethylbutyl)-4-hydroxy-2-oxo-1,2-dihydro-1,8-naphthyridine-3-carboxylate Following the procedure of Example 9b), except substituting the compound from Example 13a) for the compound from Example 9a), the title compound was obtained as a yellow oil. $^1$H NMR (400 MHz, CHLOROFORM-d) δ ppm 14.2 (s, 1H), 8.66 (d, J=2.5 Hz, 1H), 8.44 (d, J=2.5 Hz, 1H), 4.49 (q, J=7.1 Hz, 2H), 4.36-4.44 (m, 2H), 1.47-1.54 (m, 2H), 1.45 (t, J=7.2 Hz, 3H), 0.99 (s, 9H). MS(ES+) m/e 399 [M+H]⁺.

13c) N-{[6-bromo-1-(3,3-dimethylbutyl)-4-hydroxy-2-oxo-1,2-dihydro-1,8-naphthyridin-3-yl]carbonyl}glycine Following the procedure of Example 9c), except substituting the compound from Example 13b) for the compound from Example 9b), the title compound was obtained as a light cream solid following washing with methanol. $^1$H NMR (400 MHz, DMSO-$d_6$) δ ppm 12.9 (br. s., 1H), 10.4 (t, J=5.6 Hz, 1H), 8.93 (d, J=2.5 Hz, 1H), 8.53 (d, J=2.5 Hz, 1H), 4.32-4.43 (m, 2H), 4.13 (d, J=5.8 Hz, 2H), 1.42-1.54 (m, 2H), 1.00 (s, 9H). MS(ES+) m/e 426 [M+H]⁺.

Example 14

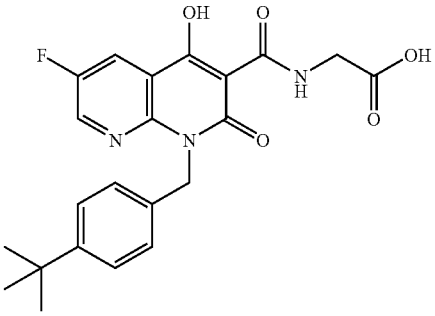

N-[(1-{[4-(1,1-dimethylethyl)phenyl]methyl}-6-fluoro-4-hydroxy-2-oxo-1,2-dihydro-1,8-naphthyridin-3-yl)carbonyl]glycine 14a) Ethyl 2-({[4-(1,1-dimethylethyl)phenyl]methyl}amino)-5-fluoro-3-pyridinecarboxylate A solution of ethyl 2-chloro-5-fluoro-3-pyridinecarboxylate (0.490 g, 2.41 mmol) in ethanol (10.0 mL) was treated with 4-tert-butylbenzylamine (0.450 mL, 2.55 mmol). The mixture was heated to 150° C. for 0.5 h and then to 160° C. for 20 min. in a Biotage Initiator microwave synthesizer. The solution was diluted with ethyl acetate and washed with saturated aqueous sodium bicarbonate. The combined organic portions were dried over magnesium sulfate, filtered, and concentrated in vacuo. Purification via flash column chromatography (20-40% ethyl acetate in hexanes) afforded a mixture of the title compound and starting material as a clear yellow oil (0.326 g, 41%). $^1$H NMR (400 MHz, CHLOROFORM-d) δ ppm 8.39 (d, J=3.0 Hz, 1H), 8.20 (d, J=3.3 Hz, 1H), 8.14 (t, J=5.1 Hz, 1H), 7.91 (dd, J=6.9, 3.2 Hz, 2H), 7.89 (dd, J=8.1, 3.0 Hz, 2H), 4.69 (d, J=5.3 Hz, 2H), 4.44 (q, J=7.1 Hz, 2H), 1.42 (t, J=7.2 Hz, 3H), 1.32 (s, 9H). MS(ES+) m/e 331 [M+H]⁺.

14b) Ethyl 1-{[4-(1,1-dimethylethyl)phenyl]methyl}-6-fluoro-4-hydroxy-2-oxo-1,2-dihydro-1,8-naphthyridine-3-carboxylate A solution of the compound from Example 14a) (0.326 g, 0.99 mmol) in dichloromethane (13.0 mL) was treated with triethylamine (0.280 mL, 2.02 mmol) followed by ethyl malonyl chloride (0.250 mL, 2.02 mmol). The mixture was stirred overnight at ambient temperature. The solution was concentrated in vacuo and the residue was dissolved in ethanol (12.0 mL). The solution was treated with sodium ethoxide (0.760 mL, 2.02 mmol, 21% solution in ethanol) at ambient temperature overnight. The solution was concentrated in vacuo and treated with water and 1N aqueous hydrochloric acid. The mixture was extracted with dichloromethane (3×20 mL). The combined organic portions were dried over magnesium sulfate, filtered, and concentrated in vacuo. Purification via flash column chromatography (40-60% ethyl acetate in hexanes) afforded the title compound as a yellow oil (0.300 g, 76%). $^1$H NMR (400 MHz, CHLOROFORM-D) δ ppm 8.54 (d, J=3.0 Hz, 1H), 8.07 (dd, J=7.8, 3.0 Hz, 1H), 7.33 (d, J=8.3 Hz, 2H), 7.22 (d, J=8.3 Hz, 2H), 5.60 (s, 2H), 4.47 (q, J=7.2 Hz, 2H), 1.42 (t, J=7.2 Hz, 3H), 1.21 (s, 9H). MS(ES+) m/e 399 [M+H]$^+$.

14c) N-[(1-{[4-(1,1-dimethylethyl)phenyl]methyl}-6-fluoro-4-hydroxy-2-oxo-1,2-dihydro-1,8-naphthyridin-3-yl)carbonyl]glycine Following the procedure of Example 9c), except substituting the compound from Example 14b) for the compound from Example 9b), the title compound was obtained as a brown solid. $^1$H NMR (400 MHz, DMSO-d$_6$) δ ppm 10.4 (t, J=5.6 Hz, 1H), 8.88 (d, J=2.8 Hz, 1H), 8.36 (dd, J=8.0, 2.9 Hz, 1H), 7.30 (d, J=8.6 Hz, 2H), 7.19 (d, J=8.3 Hz, 2H), 5.59 (s, 2H), 4.14 (d, J=5.6 Hz, 2H), 1.23 (s, 9H). MS(ES+) m/e 428 [M+H]$^+$.

Example 15

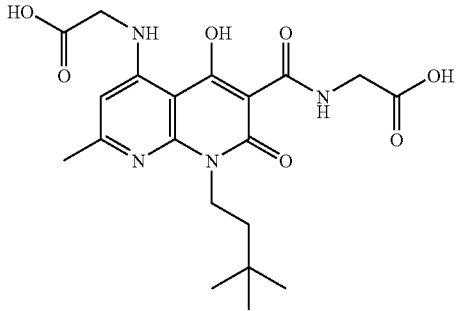

{[6-{[(Carboxymethyl)amino]carbonyl}-8-(3,3-dimethylbutyl)-5-hydroxy-2-methyl-7-oxo-7,8-dihydro-1,8-naphthyridin-4-yl]amino}acetic acid

15a) Ethyl 4-chloro-2-[(3,3-dimethylbutyl)amino]-6-methyl-3-pyridinecarboxylate Following the procedure of Example 12a), except substituting ethyl 2,4-dichloro-6-methyl-3-pyridinecarboxylate for ethyl 2-chloro-5-fluoro-3-pyridinecarboxylate, the title compound was obtained as a clear oil following purification via flash column chromatography (10% ethyl acetate in hexanes). $^1$H NMR (400 MHz, CHLOROFORM-d) δ ppm 7.29 (br. s., 1H), 6.45 (s, 1H), 4.38 (q, J=7.2 Hz, 2H), 3.41-3.54 (m, 2H), 2.36 (s, 3H), 1.49-1.61 (m, 2H), 1.41 (t, J=7.1 Hz, 3H), 0.98 (s, 9H). MS(ES+) m/e 299 [M+H]$^+$.

15b) Ethyl 5-chloro-1-(3,3-dimethylbutyl)-4-hydroxy-7-methyl-2-oxo-1,2-dihydro-1,8-naphthyridine-3-carboxylate Following the procedure of Example 14b), except substituting the compound in Example 15a) for the compound in Example 14a), the title compound was obtained as an orange oil. $^1$H NMR (400 MHz, CHLOROFORM-D) δ ppm 7.02 (s, 1H), 4.47 (q, J=7.1 Hz, 2H), 4.41-4.44 (m, 2H), 2.52 (s, 3H), 1.47-1.53 (m, 2H), 1.43 (t, J=7.1 Hz, 3H), 0.99 (s, 1H). MS(ES+) m/e 367 [M+H]$^+$.

15c) {[6-{[(carboxymethyl)amino]carbonyl}-8-(3,3-dimethylbutyl)-5-hydroxy-2-methyl-7-oxo-7,8-dihydro-1,8-naphthyridin-4-yl]amino}acetic acid Following the procedure of Example 9c), except substituting the compound in Example 15b) for the compound in Example 9b), the title compound was obtained as a pale brown solid. $^1$H NMR (400 MHz, DMSO-d$_6$) δ ppm 10.7 (t, J=5.6 Hz, 1H), 8.53 (t, J=5.1 Hz, 1H), 6.30 (s, 1H), 4.34-4.42 (m, 2H), 4.13 (d, J=5.6 Hz, 2H), 4.10 (d, J=5.1 Hz, 2H), 2.37 (s, 3H), 1.42-1.55 (m, 2H), 1.00 (s, 9H). MS(ES+) m/e 435 [M+H]$^+$.

Example 16

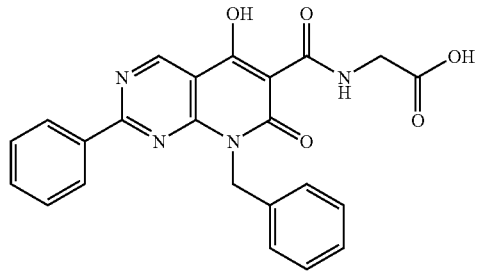

N-{[5-hydroxy-7-oxo-2-phenyl-8-(phenylmethyl)-7,8-dihydropyrido[2,3-d]pyrimidin-6-yl]carbonyl}glycine

16a) Ethyl 3-oxo-3-[(phenylmethyl)amino]propanoate

A solution of benzylamine (1.10 g, 10.3 mmol) and ethyl malonyl chloride (1.29 mL, 10.3 mmol) in dichloromethane (10 mL) was treated with triethylamine (1.44 mL, 10.3 mmol). The solution was stirred at ambient temperature for 1 h and then diluted with saturated aqueous sodium bicarbonate and extracted with ethyl acetate (3×20 mL). The combined organic portions were dried over magnesium sulfate, filtered, and concentrated in vacuo to obtain the title compound as a yellow oil (2.27 g, 100%). $^1$H NMR (400 MHz, CHLOROFORM-d) δ ppm 7.55 (br. s., 1H), 7.24-7.36 (m, 5H), 4.45 (d, J=5.6 Hz, 2H), 4.17 (q, J=7.2 Hz, 2H), 3.31 (s, 2H), 1.27 (t, J=7.2 Hz, 3H). MS(ES+) m/e 222 [M+H]$^+$.

16b) Ethyl 5-hydroxy-7-oxo-2-phenyl-8-(phenylmethyl)-7,8-dihydropyrido[2,3-d]pyrimidine-6-carboxylate A solution of ethyl 4-chloro-2-phenyl-5-pyrimidinecarboxylate (0.130 g, 0.51 mmol) in tetrahydrofuran (12.0 mL) was treated with the compound from Example 16a) (0.110 g, 0.51 mmol) followed by potassium carbonate (0.070 g, 0.51 mmol) and copper bromide (0.008 g, 0.04 mmol). The mixture was stirred at ambient temperature for 10 minutes and then under reflux overnight. The solution was cooled to ambient temperature and poured into 1N aqueous hydrogen chloride. The organic layer was separated and the aqueous layer was extracted with ethyl acetate (3×10 mL). The combined organic portions were dried over magnesium sulfate, filtered, and concentrated in vacuo. The title compound was obtained as a yellow solid following washing with ethyl acetate and hexanes (0.135 g, 66%). $^1$H NMR (400 MHz, CHLOROFORM-d) δ ppm 15.6 (br. s., 1H), 9.17 (s, 1H), 8.44-8.63 (m, 1H), 8.26 (d, J=7.6 Hz, 2H), 7.69-7.78 (m, 1H), 7.66 (t, J=7.5 Hz, 2H), 7.49-7.55 (m, 2H), 7.28-7.35 (m, 2H), 7.19-7.26 (m, 1H), 5.27 (s, 2H), 4.49 (q, J=7.2 Hz, 2H), 1.48 (t, J=7.1 Hz, 3H). MS(ES+) m/e 401 [M+H]$^+$.

16c) N-{[5-hydroxy-7-oxo-2-phenyl-8-(phenylmethyl)-7,8-dihydropyrido[2,3-d]pyrimidin-6-yl]carbonyl}glycine Glycine sodium salt (0.006 g, 0.06 mmol) was added to a solution of the compound from Example 16b) (0.020 g, 0.06 mmol) in ethanol (2.0 mL). The mixture was heated to 150° C. for 15 min. followed by 160° C. for 1 h in a Biotage Initiator microwave synthesizer. The reaction was quenched with 1 N aqueous hydrochloric acid and extracted with ethyl acetate (3×10 mL). The combined organic portions were dried over magnesium sulfate, filtered, concentrated in vacuo, and purified via flash column chromatography (40-60% ethyl acetate in hexanes) to afford the title compound as a yellow solid (0.001 g, 4%). $^1$H NMR (400 MHz, DMSO-d$_6$) δ ppm 9.99 (t, J=5.3 Hz, 1H), 9.15 (s, 1H), 8.21 (d, J=6.3 Hz, 2H), 7.66-7.88 (m, 3H), 7.21-7.34 (m, 5H), 5.17 (s, 2H), 4.11 (d, J=5.3 Hz, 2H). MS(ES+) m/e 431 [M+H]$^+$.

Example 17

N-[(1-{[4-(1,1-dimethylethyl)phenyl]methyl}-4-hydroxy-2-oxo-1,2-dihydro-1,8-naphthyridin-3-yl)carbonyl]glycine

17a) Ethyl 2-({[4-(1,1-dimethylethyl)phenyl]methyl}amino)-3-pyridinecarboxylate A solution of ethyl 2-chloro-3-pyridinecarboxylate (0.610 g, 3.29 mmol) in ethanol (10.0 mL) was treated with 4-tert-butylbenzylamine (0.580 mL, 3.29 mmol). The mixture was heated to 160° C. for 1 h in a Biotage Initiator microwave synthesizer. The solution was diluted with ethyl acetate and washed with saturated aqueous sodium bicarbonate. The organic portion was dried over magnesium sulfate, filtered, and concentrated in vacuo. Purification via flash column chromatography (20-60% ethyl acetate in hexanes) afforded the title compound clear yellow oil (0.461 g, 45%). $^1$H NMR (400 MHz, CHLOROFORM-d) δ ppm 8.34 (dd, J=4.8, 1.8 Hz, 1H), 8.18 (dd, J=7.8, 2.0 Hz, 1H), 7.30-7.42 (m, 4H), 6.58 (dd, J=7.6, 4.8 Hz, 1H), 4.75 (d, J=5.6 Hz, 2H), 4.34 (q, J=7.1 Hz, 2H), 1.39 (t, J=7.2 Hz, 3H), 1.34 (s, 9H). MS(ES+) m/e 313 [M+H]$^+$.

17b) Ethyl 1-{[4-(1,1-dimethylethyl)phenyl]methyl}-4-hydroxy-2-oxo-1,2-dihydro-1,8-naphthyridine-3-carboxylate Following the procedure of Example 9b), except substituting the compound from Example 17a) for the compound from Example 9a), the title compound was obtained as a white solid (0.127 g, 23%). $^1$H NMR (400 MHz, CHLOROFORM-d) δ ppm 14.3 (br. s., 1H), 8.73 (dd, J=4.5, 2.0 Hz, 1H), 8.45 (dd, J=8.0, 1.9 Hz, 1H), 7.40 (d, J=8.6 Hz, 2H), 7.29 (s, 1H), 7.22 (dd, J=7.8, 4.5 Hz, 1H), 5.70 (s, 2H), 4.54 (q, J=7.1 Hz, 2H), 1.65 (s, 2H), 1.50 (t, J=7.2 Hz, 3H), 1.28 (s, 9H). MS(ES+) m/e 381 [M+H]$^+$.

17c) N-[(1-{[4-(1,1-dimethylethyl)phenyl]methyl}-4-hydroxy-2-oxo-1,2-dihydro-1,8-naphthyridin-3-yl)carbonyl]glycine Glycine sodium salt (0.030 g, 0.35 mmol) was added to a solution of the compound from Example 17b) (0.130 g, 0.33 mmol) in ethanol (2.0 mL). The mixture was heated to 160° C. for 1 h in a Biotage Initiator microwave synthesizer. The reaction was quenched with 6N aqueous hydrochloric acid and the resulting precipitate was filtered, washed with water, and dried in vacuo to afford the title compound as an off-white solid (0.090 g, 68%). $^1$H NMR (400 MHz, DMSO-d$_6$) δ ppm 10.4 (t, J=5.6 Hz, 1H), 8.81 (dd, J=4.7, 1.9 Hz, 1H), 8.51 (dd, J=7.8, 1.8 Hz, 1H), 7.46 (dd, J=8.0, 4.7 Hz, 1H), 7.27-7.33 (m, 2H), 7.17-7.22 (m, 2H), 5.62 (s, 2H), 4.12 (d, J=5.6 Hz, 2H), 1.23 (s, 9H). MS(ES+) m/e 410 [M+H]$^+$.

Example 18

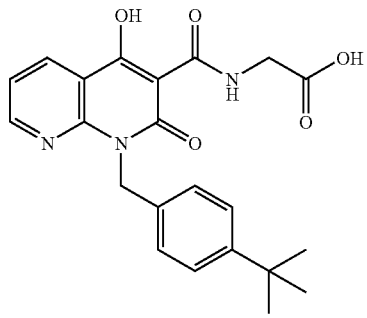

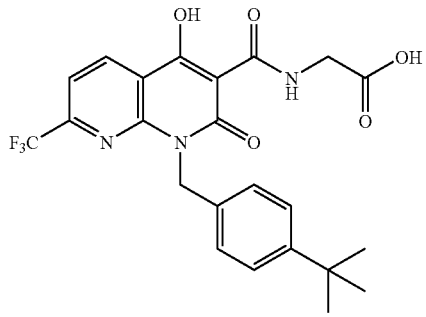

N-{1-{[4-(1,1-dimethylethyl)phenyl]methyl}-4-hydroxy-2-oxo-7-(trifluoromethyl)-1,2-dihydro-1,8-naphthyridin-3-yl]carbonyl}glycine

18a) Ethyl 2-({[4-(1,1-dimethylethyl)phenyl]methyl}amino)-6-(trifluoromethyl)-3-pyridinecarboxylate Following the procedure of Example 9a), except substituting 2-chloro-6-(trifluoromethyl)-3-pyridinecarboxylic acid for 2-chloro-6-methylnicotinic acid and 4-tert-butylbenzylamine for (3,3-dimethylbutyl)amine, the title compound was obtained as a creamy yellow solid. $^1$H NMR (400 MHz, CHLOROFORM-d) δ ppm 8.41 (s, 1H), 8.27 (d, J=7.8 Hz, 1H), 7.30-7.38 (m, 4H), 6.88 (d, J=7.8 Hz, 1H), 4.73 (d, J=5.6 Hz, 2H), 4.35 (q, J=7.1 Hz, 2H), 1.39 (t, J=7.1 Hz, 3H), 1.33 (s, 9H). MS(ES+) m/e 381 [M+H]$^+$.

18b) Ethyl 1-{[4-(1,1-dimethylethyl)phenyl]methyl}-4-hydroxy-2-oxo-7-(trifluoromethyl)-1,2-dihydro-1,8-naphthyridine-3-carboxylate A solution of the compound from Example 18a) (0.760 g, 1.99 mmol) in dichloromethane (25.0 mL) was treated with triethylamine (1.39 mL, 9.95 mmol) followed by ethyl malonyl chloride (1.25 mL, 9.95 mmol). The mixture was stirred at ambient temperature overnight. The mixture was once again treated with the same amount of triethylamine and ethyl malonyl chloride and stirred at ambient temperature for an additional 2 h. The solution was concentrated in vacuo and the residue was dissolved in ethanol (12.0 mL). The solution was treated with sodium ethoxide (3.71 mL, 9.95 mmol, 21% solution in ethanol) at ambient temperature and stirred overnight. The solution was concentrated in vacuo and treated with water and 1N aqueous hydrochloric acid. The mixture was extracted with (3×20 mL) ethyl acetate. The combined organic portions were dried over magnesium sulfate, filtered, and concentrated in vacuo. Purification via flash column chromatography (40-60% ethyl acetate in hexanes) afforded the title compound as a white solid (0.300 g, 34%). $^1$H NMR (400 MHz, CHLOROFORM-d) δ ppm 14.3 (s, 1H), 8.60 (d, J=7.6 Hz, 1H), 7.59 (d, J=8.6 Hz, 2H), 7.55 (d, J=8.1 Hz, 1H), 7.31 (d, J=8.3 Hz, 2H), 5.65 (s, 2H), 4.57 (q, J=7.1 Hz, 2H), 1.52 (t, J=7.1 Hz, 3H), 1.28 (s, 9H). MS(ES+) m/e 449 [M+H]$^+$.

18c) N-{1-{[4-(1,1-dimethylethyl)phenyl]methyl}-4-hydroxy-2-oxo-7-(trifluoromethyl)-1,2-dihydro-1,8-naphthyridin-3-yl]carbonyl}glycine Following the procedure of Example 17c), except substituting the compound from Example 18b) for the compound from Example 17b), the title compound was obtained as a pale peach solid. $^1$H NMR (400 MHz, DMSO-d$_6$) δ ppm 10.3 (t, J=5.6 Hz, 1H), 8.74 (d, J=8.1 Hz, 1H), 7.89 (d, J=8.1 Hz, 1H), 7.29-7.34 (m, 4H), 5.55 (s, 2H), 4.15 (d, J=5.6 Hz, 2H), 1.28 (s, 9H). MS(ES+) m/e 478 [M+H]$^+$.

Example 19

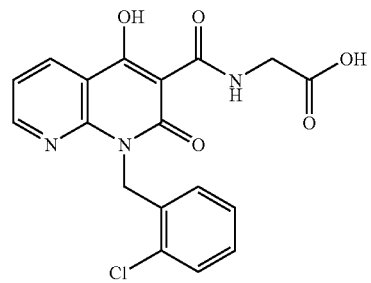

N-({1-[(2-chlorophenyl)methyl]-4-hydroxy-2-oxo-1,2-dihydro-1,8-naphthyridin-3-yl}carbonyl)glycine

19a) Ethyl 2-{[(2-chlorophenyl)methyl]amino}-3-pyridinecarboxylate

Following the procedure of Example 17a), except substituting 2-chlorobenzylamine for 4-tert-butylbenzylamine, the title compound was obtained as clear crystals. $^1$H NMR (400 MHz, CHLOROFORM-d) δ ppm 8.43 (br. s., 1H), 8.29 (dd, J=4.8, 2.0 Hz, 1H), 8.16 (dd, J=7.8, 2.0 Hz, 1H), 7.41-7.47 (m, 1H), 7.36-7.40 (m, 1H), 7.17-7.24 (m, 2H), 6.57 (dd, J=7.6, 4.8 Hz, 1H), 4.88 (d, J=6.1 Hz, 2H), 4.35 (q, J=7.1 Hz, 2H), 1.39 (t, J=7.2 Hz, 3H). MS(ES+) m/e 291 [M+H]$^+$.

19b) Ethyl 1-[(2-chlorophenyl)methyl]-4-hydroxy-2-oxo-1,2-dihydro-1,8-naphthyridine-3-carboxylate Following the procedure of Example 18b), except substituting the compound from Example 19a) for the compound in Example 18a), the title compound was obtained as a pink solid. $^1$H NMR (400 MHz, CHLOROFORM-d) δ ppm 14.4 (s, 1H), 8.64 (dd, J=4.7, 1.9 Hz, 1H), 8.50 (dd, J=8.0, 1.9 Hz, 1H), 7.40 (dd, J=8.0, 1.1 Hz, 1H), 7.24 (dd, J=7.8, 4.8 Hz, 1H), 7.15 (td, J=7.6, 1.6 Hz, 1H), 7.06 (td, J=7.6, 1.3 Hz, 1H), 6.68 (dd, J=7.6, 1.3 Hz, 1H), 5.80 (s, 2H), 4.53 (q, J=7.2 Hz, 2H), 1.49 (t, J=7.2 Hz, 3H). MS(ES+) m/e 359 [M+H]$^+$.

19c) N-({1-[(2-chlorophenyl)methyl]-4-hydroxy-2-oxo-1,2-dihydro-1,8-naphthyridin-3-yl}carbonyl)glycine Following the procedure of Example 17c), except substituting the compound from Example 19b) for the compound in Example 17b), the title compound was obtained as a tan solid. $^1$H NMR (400 MHz, DMSO-d$_6$) δ ppm 13.0 (br. s., 1H), 10.3 (t, J=5.4 Hz, 1H), 8.74 (dd, J=4.7, 1.9 Hz, 1H), 8.54 (dd, J=8.0, 1.9 Hz, 1H), 7.51 (dd, J=7.8, 1.0 Hz, 1H), 7.46 (dd, J=8.0, 4.7 Hz, 1H), 7.26 (td, J=7.6, 1.5 Hz, 1H), 7.14 (td, J=7.6, 1.0 Hz, 1H), 6.71 (d, J=6.8 Hz, 1H), 5.65 (s, 2H), 4.12 (d, J=5.6 Hz, 2H). MS(ES+) m/e 388 [M+H]$^+$.

Example 20

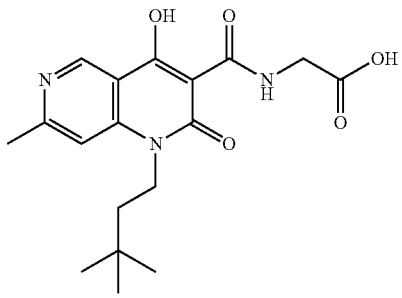

N-{[1-(3,3-dimethylbutyl)-4-hydroxy-7-methyl-2-oxo-1,2-dihydro-1,6-naphthyridin-3-yl]carbonyl}glycine

20a) Ethyl 2-chloro-4-[(3,3-dimethylbutyl)amino]-6-methyl-3-pyridinecarboxylate A solution of ethyl 2,4-dichloro-6-methyl-3-pyridinecarboxylate (1.00 g, 4.27 mmol) in ethanol (20.0 mL) was treated with (3,3-dimethylbutyl)amine (0.570 mL, 4.27 mmol). The mixture was refluxed for 2 days, and upon cooling, diluted with ethyl acetate and washed with saturated aqueous sodium bicarbonate. The aqueous layer was extracted twice with ethyl acetate. The combined organic portions were dried over magnesium sulfate, filtered, concentrated in vacuo, and purified via flash column chromatography (20-60% ethyl acetate in hexanes) to afford the title compound as an amber oil (1.02 g, 80%). $^1$H NMR (400 MHz, CHLOROFORM-d) δ ppm 6.94 (t, J=4.4 Hz, 1H), 6.18 (s, 1H), 4.23 (q, J=7.2 Hz, 2H), 2.82-3.17 (m, 2H), 2.25 (s, 3H), 1.35-1.54 (m, 2H), 1.25 (t, J=7.1 Hz, 3H), 0.84 (s, 9H). MS(ES+) m/e 299 [M+H]$^+$.

20b) Ethyl 5-chloro-1-(3,3-dimethylbutyl)-4-hydroxy-7-methyl-2-oxo-1,2-dihydro-1,6-naphthyridine-3-carboxylate Following the procedure of Example 9b), except substituting the compound from Example 20a) for the compound of Example 9a), the title compound was obtained as a yellow oil. $^1$H NMR (400 MHz, CHLOROFORM-d) δ ppm 15.2 (s, 1H), 6.91 (s, 1H), 4.53 (q, J=7.2 Hz, 2H), 4.16-4.26 (m, 2H), 2.62 (s, 3H), 1.52-1.61 (m, 2H), 1.48 (t, J=7.2 Hz, 3H), 1.08 (s, 9H). MS(ES+) m/e 367 [M+H]$^+$.

20c) Ethyl 1-(3,3-dimethylbutyl)-4-hydroxy-7-methyl-2-oxo-1,2-dihydro-1,6-naphthyridine-3-carboxylate A solution of the compound from Example 20b) (0.560 g, 1.51 mmol) in ethanol (25.0 mL) was treated with palladium on carbon (0.161 g, 10% w/w, 0.151 mmol) and potassium hydroxide (0.080 g, 1.51 mmol). The hydrogenation was carried out under 55 psi of hydrogen for 2 days. The catalyst was removed by filtration through a celite pad. The filtrate was concentrated in vacuo, diluted with water, and extracted twice with dichloromethane. The combined organic portions were dried over magnesium sulfate, filtered, and concentrated in vacuo to obtain the title compound as a yellow oil (0.172 g, 34%). $^1$H NMR (400 MHz, METHANOL-d$_4$) δ ppm 9.08 (s, 1H), 7.03 (br. s., 1H), 4.33 (br. s., 2H), 4.15 (br. s., 2H), 3.61 (q, J=7.1 Hz, 2H), 2.58 (s, 3H), 1.18 (t, J=7.1 Hz, 3H), 0.90 (s, 9H). MS(ES+) m/e 333 [M+H]$^+$.

20d) N-{[1-(3,3-dimethylbutyl)-4-hydroxy-7-methyl-2-oxo-1,2-dihydro-1,6-naphthyridin-3-yl]carbonyl}glycine Following the procedure of Example 9c), except substituting the compound from Example 20c) for the compound from Example 9b), the title compound was obtained as a beige solid. $^1$H NMR (400 MHz, DMSO-d$_6$) δ ppm 10.3 (t, J=5.6 Hz, 1H), 9.07 (s, 1H), 7.25 (s, 1H), 4.15-4.30 (m, 2H), 4.09 (d, J=5.6 Hz, 2H), 2.63 (s, 3H), 1.36-1.60 (m 2H), 1.04 (s, 9H). MS(ES+) m/e 362 [M+H]$^+$.

Example 21

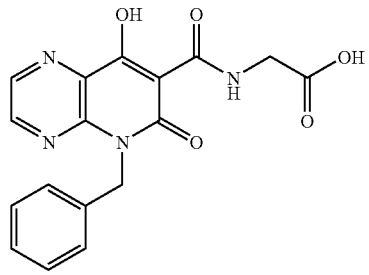

N-{[8-hydroxy-6-oxo-5-(phenylmethyl)-5,6-dihydropyrido[2,3-b]pyrazin-7-yl]carbonyl}glycine

21a) Ethyl 8-hydroxy-6-oxo-5,6-dihydropyrido[2,3-]pyrazine-7-carboxylate

A solution of 3-aminopyrazine-2-carboxylic acid methyl ester (0.596 g, 3.89 mmol) in dichloromethane (20.0 mL) was treated with triethylamine (2.65 mL, 19.40 mmol) followed by ethyl malonyl chloride (2.44 mL, 19.40 mmol). The mixture was stirred at ambient temperature overnight. The solution was concentrated in vacuo and the residue was dissolved in ethanol (15.0 mL). The solution was treated with sodium ethoxide (7.20 mL, 19.40 mmol, 21% solution in ethanol) at ambient temperature and stirred for 2 h. The solution was dissolved with water and treated with 6N aqueous hydrochloric acid. The solid formed was filtered and washed with diethyl ether to afford the title compound as a yellow solid (0.667 g, 73%). $^1$H NMR (400 MHz, DMSO-d$_6$) δ ppm 12.3 (s, 1H), 8.68 (d, J=2.3 Hz, 1H), 8.57 (d, J=2.3 Hz, 1H), 4.26 (q, J=7.2 Hz, 2H), 1.27 (t, J=7.1 Hz, 3H). MS(ES+) m/e 235 [M+H]$^+$.

21b) Ethyl 8-hydroxy-6-oxo-5-(phenylmethyl)-5,6-dihydropyrido[2,3-b]pyrazine-7-carboxylate A solution of the compound from Example 21a) (0.120 g, 0.51 mmol) in N,N-dimethylformamide (10.0 mL) was treated with sodium hydride (0.040 g, 1.02 mmol, 60% mineral oil dispersion) at ambient temperature for 1 h. Benzyl bromide (0.060 mL, 0.51 mmol) was then added via syringe and the reaction was heated to 78° C. overnight. Upon cooling, the solution was diluted with water and treated with 6N hydrochloric acid. A precipitate was filtered and the mother liquor was extracted with ethyl acetate, dried over magnesium sulfate, filtered, and concentrated in vacuo. The residue was purified via flash column chromatography (20-60% ethyl acetate in hexanes) to afford the title compound as a dark red solid (0.090 g, 60%). $^1$H NMR (400 MHz, CHLOROFORM-d) δ ppm 14.2 (s, 1H), 8.67 (d, J=2.3 Hz, 1H), 8.60 (d, J=2.3 Hz, 1H), 7.45 (d, J=6.8 Hz, 1H), 7.21-7.32 (m, 4H), 5.65 (s, 2H), 4.56 (q, J=7.1 Hz, 2H), 1.50 (t, J=7.1 Hz, 3H). MS(ES+) m/e 326 [M+H]$^+$.

21c) N-{[8-hydroxy-6-oxo-5-(phenylmethyl)-5,6-dihydropyrido[2,3-b]pyrazin-7-yl]carbonyl}glycine Following the procedure of Example 9c), except substituting the compound from Example 21b) for the compound from Example 9b), the title compound was obtained as a yellow powder. $^1$H NMR (400 MHz, DMSO-d$_6$) δ ppm 10.4 (t, J=5.6 Hz, 1H), 8.84 (d, J=2.3 Hz, 1H), 8.74 (d, J=2.3 Hz, 1H), 7.25-7.30 (m, 4H), 7.17-7.25 (m, 1H), 5.59 (s, 2H), 4.13 (d, J=5.8 Hz, 2H). MS(ES+) m/e 355 [M+H]$^+$.

Example 22

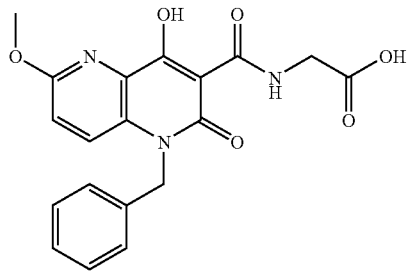

N-{[4-hydroxy-6-(methyloxy)-2-oxo-1-(phenylmethyl)-1,2-dihydro-1,5-naphthyridin-3-yl]carbonyl}glycine 22a) 6-(methyloxy)-N-(phenylmethyl)-3-pyridinamine A solution of 5-amino-2-methoxypyridine (1.00 g, 8.06 mmol) in dichloromethane (20.0 mL) was treated with benzaldehyde (0.080 mL, 8.06 mmol) followed by stirring at ambient temperature for 20 min. The mixture was then treated with sodium cyanoborohydride (1.79 g, 8.46 mmol) followed by acetic acid (0.460 mL, 8.06) and continued stirring for 2 h. The solution was treated with water and saturated sodium hydrogen carbonate, and then extracted twice with dichloromethane. The combined organic portions were dried over magnesium sulfate, filtered, and concentrated in vacuo. The resulting oil was swirled in hexanes, and a solid was filtered. The filtrate was concentrated and the title compound was obtained as a light pink solid (0.340 g, 20%). $^1$H NMR (400 MHz, CHLOROFORM-d) δ ppm 7.61 (d, J=2.5 Hz, 1H), 7.28-7.41 (m, 5H), 7.01 (dd, J=8.8, 3.0 Hz, 1H), 6.62 (d, J=9.3 Hz, 1H), 4.30 (s, 2H), 3.87 (s, 3H). MS(ES+) m/e 215 [M+H]$^+$.

22b) Ethyl 4-hydroxy-6-(methyloxy)-2-oxo-1-(phenylmethyl)-1,2-dihydro-1,5-naphthyridine-3-carboxylate A microwave vial was charged with the compound from Example 22a) (0.340 g, 1.58 mmol), triethyl methanetricarboxylate (1.00 mL, 4.77 mmol) and 1,4-dioxane (5.0 mL). The solution was heated to 240° C. for 2 h in a Biotage Initiator microwave synthesizer. The contents were concentrated in vacuo and the residue was purified via flash column chromatography (20-60% ethyl acetate in hexanes). A mixture of compounds was obtained. This mixture was washed with hexanes, a solid was filtered and washed with methanol, to afford the title compound as a light yellow solid (0.050 g, 15%). $^1$H NMR (400 MHz, DMSO-d$_6$) δ ppm 7.83 (d, J=9.3 Hz, 1H), 7.28-7.38 (m, 2H), 7.25 (d, J=7.1 Hz, 1H), 7.17 (d, J=7.1 Hz, 2H), 7.13 (d, J=9.1 Hz, 1H), 5.45 (s, 2H), 4.31 (q, J=7.1 Hz, 2H), 3.99 (s, 3H), 1.30 (t, J=7.1 Hz, 3H). MS(ES+) m/e 355 [M+H]$^+$.

22c) N-{[4-hydroxy-6-(methyloxy)-2-oxo-1-(phenylmethyl)-1,2-dihydro-1,5-naphthyridin-3-yl]carbonyl}glycine Following the procedure of Example 17c), except substituting the compound from Example 22b) for the compound from Example 17b), the title compound was obtained as a yellow solid. $^1$H NMR (400 MHz, DMSO-d$_6$) δ ppm 10.6 (t, J=5.4 Hz, 1H), 7.90 (d, J=9.1 Hz, 1H), 7.31 (t, J=7.3 Hz, 2H), 7.15-7.27 (m, 4H), 5.25 (br. s., 2H), 4.15 (d, J=5.6 Hz, 2H), 3.93 (s, 3H). MS(ES+) m/e 383 [M+H]$^+$.

Example 23

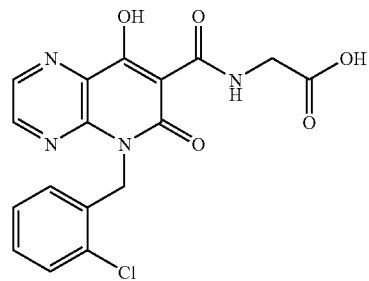

N-({5-[(2-chlorophenyl)methyl]-8-hydroxy-6-oxo-5,6-dihydropyrido[2,3-b]pyrazin-7-yl}carbonyl)glycine 23a) Ethyl 5-[(2-chlorophenyl)methyl]-8-hydroxy-6-oxo-5,6-dihydropyrido[2,3-b]pyrazine-7-carboxylate Following the procedure of Example 21b), except substituting 2-chlorobenzyl bromide for benzyl bromide, the title compound was obtained as an orange solid following purification via flash column chromatography (0-10% methanol in dichloromethane). $^1$H NMR (400 MHz, DMSO-d$_6$) δ ppm 8.63 (m, 1H), 7.49 (d, J=7.6 Hz, 1H), 7.29-7.42 (m, 1H), 7.26 (t, J=7.5 Hz, 1 H), 7.16 (t, J=7.6 Hz, 1H), 6.51-6.79 (m, 1H), 5.48 (s, 2H), 4.22 (q, J=7.1 Hz, 2H), 1.25 (t, J=7.1 Hz, 3H). MS(ES+) m/e 360 [M+H]$^+$.

23b) N-({5-[(2-chlorophenyl)methyl]-8-hydroxy-6-oxo-5,6-dihydropyrido[2,3-b]pyrazin-7-yl}carbonyl)glycine Following the procedure of Example 17c), except substituting the compound from Example 23a) for the compound from Example 17b), the title compound was obtained as a red orange solid. $^1$H NMR (400 MHz, DMSO-$d_6$) δ ppm 10.3 (t, J=4.9 Hz, 1H), 8.79 (d, J=2.3 Hz, 1H), 8.75 (d, J=2.3 Hz, 1H), 7.51 (dd, J=8.0, 1.1 Hz, 1H), 7.27 (td, J=7.7, 1.5 Hz, 1H), 7.14 (td, J=7.6, 1.3 Hz, 1H), 6.87 (dd, J=7.8, 1.3 Hz, 1H), 5.58 (s, 2H), 4.13 (d, J=5.6 Hz, 2H). MS(ES+) m/e 389 [M+H]$^+$.

Example 24

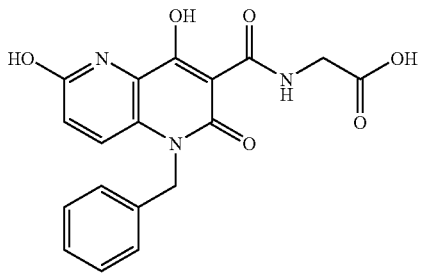

N-{[4-hydroxy-2,6-dioxo-1-(phenylmethyl)-1,2,5,6-tetrahydro-1,5-naphthyridin-3-yl]carbonyl}glycine A solution of the compound from Example 22c) (0.014 g, 0.037 mmol) in dichloromethane (2 mL) was treated with iodotrimethylsilane (0.005 mL, 1.10 mmol) at ambient temperature. The solution was stirred for 1 h and then treated with water followed by methanol. The solvent was removed in vacuo and the residue was taken up in ethyl acetate and washed with saturated aqueous sodium bicarbonate and brine. The organic phase was dried over magnesium sulfate, filtered, and concentrated in vacuo to afford the title compound as a yellow solid (0.009 g, 66%). $^1$H NMR (400 MHz, DMSO-$d_6$) δ ppm 10.6 (t, J=5.3 Hz, 1H), 7.80 (d, J=9.9 Hz, 1H), 7.33 (t, J=7.3 Hz, 2H), 7.25 (t, J=7.2 Hz, 1H), 7.19 (d, J=7.1 Hz, 2H), 6.90 (d, J=8.6 Hz, 1H), 5.51 (br. s., 2H), 4.14 (d, J=5.3 Hz, 2H). MS(ES+) m/e 370 [M+H]$^+$.

Biological Background:

The following references set out information about the target enzymes, HIF prolyl hydroxylases, and methods and materials for measuring inhibition of same by small molecules.

M. Hirsilä, P. Koivunen, V. Günzler, K. I. Kivirikko, and J. Myllyharju "Characterization of the Human Prolyl 4-Hydroxylases That Modify the Hypoxia-inducible Factor" *J. Biol. Chem.*, 2003, 278, 30772-30780.

C. Willam, L. G. Nicholls, P. J. Ratcliffe, C. W. Pugh, P. H. Maxwell "The prolyl hydroxylase enzymes that act as oxygen sensors regulating destruction of hypoxia-inducible factor α" *Advan. Enzyme Regul.*, 2004, 44, 75-92

M. S. Wiesener, J. S. Jürgensen, C. Rosenberger, C. K. Scholze, J. H. Hörstrup, C. Warnecke, S. Mandriota, I. Bechmann, U. A. Frei, C. W. Pugh, P. J. Ratcliffe, S. Bachmann, P. H. Maxwell, and K.-U. Eckardt "Widespread hypoxia-inducible expression of HIF-2α in distinct cell populations of different organs" *FASEB J.*, 2003, 17, 271-273.

S. J. Klaus, C. J. Molineaux, T. B. Neff, V. Guenzler-Pukall, I. Lansetmo Parobok, T. W. Seeley, R. C. Stephenson "Use of hypoxia-inducible factor α(HIFα) stabilizers for enhancing erythropoiesis" PCT Int. Appl. (2004), WO 2004108121 A1

C. Warnecke, Z. Zaborowska, J. Kurreck, V. A. Erdmann, U. Frei, M. Wiesener, and K.-U. Eckardt "Differentiating the functional role of hypoxia-inducible factor (HIF)-1α and HIF-2α (EPAS-1) by the use of RNA interference: erythropoietin is a HIF-2α target gene in Hep3B and Kelly cells" *FASEB J.*, 2004, 18, 1462-1464.

For the Expression of EGLN3 see:

R. K. Bruick and S. L. McKnight "A Conserved Family of Prolyl-4-Hydroxylases That Modify HIF" *Science*, 2001, 294, 1337-1340.

For the Expression of HIF2α-CODD see:

a) P. Jaakkola, D. R. Mole, Y.-M. Tian, M. I. Wilson, J. Gielbert, S. J. Gaskell, A. von Kriegsheim, H. F. Hebestreit, M. Mukherji, C. J. Schofield, P. H. Maxwell, C. W. Pugh, P, J. Ratcliffe "Targeting of HIF-α to the von Hippel-Lindau Ubiquitylation Complex by $O_2$-Regulated Prolyl Hydroxylation" *Science*, 2001, 292, 468-472.

b) M. Ivan, K. Kondo, H. Yang, W. Kim, J. Valiando, M. Ohh, A. Salic, J. M. Asara, W. S. Lane, W. G. Kaelin Jr. "HIFα Targeted for VHL-Mediated Destruction by Proline Hydroxylation: Implications for $O_2$Sensing" *Science*, 2001, 292, 464-468.

For the Expression of VHL, Elongin b and Elongin c See:

A. Pause, S. Lee, R. A. Worrell, D. Y. T. Chen, W. H. Burgess, W. M. Linehan, R. D. Klausner "The von Hippel-Lindau tumor-suppressor gene product forms a stable complex with human CUL-2, a member of the Cdc53 family of proteins" *Proc. Natl. Acad. Sci. USA*, 1997, 94, 2156-2161.

Biological Assay(s)

EGLN3 Assay

Materials:

His-MBP-EGLN3 (6HisMBPAttB1EGLN3(1-239)) was expressed in *E. Coli* and purified from an amylase affinity column. Biotin-VBC [6HisSumoCysVHL(2-213), 6HisSumoElonginB(1-118), and 6His SumoElonginC(1-112)] and His-GB1-HIF2α-CODD (6HisGB1tevHIF2A (467-572)) were expressed from *E. Coli*.

Method:

Cy5-labelled HIF2α CODD, and a biotin-labeled VBC complex were used to determine EGLN3 inhibition. EGLN3 hydroxylation of the Cy5CODD substrate results in its recognition by the biotin-VBC. Addition of a Europium/streptavidin (Eu/SA) chelate results in proximity of Eu to Cy5 in the product, allowing for detection by energy transfer. A ratio of Cy5 to Eu emission (LANCE Ratio) is the ultimate readout, as this normalized parameter has significantly less variance than the Cy5 emission alone.

Then 50 nL of inhibitors in DMSO (or DMSO controls) were stamped into a 384-well low volume Corning NBS plate, followed by addition of 2.5 μL of enzyme [50 mL buffer (50 mM HEPES/50 mM KCl)+1 mL of a 10 mg/mL BSA in buffer+6.25 μL of a 10 mg/mL $FeCl_2$ solution in water+100 μL of a 200 mM solution of ascorbic acid in water+15.63 μL EGLN3] or control [50 mL buffer+1 mL of a 10 mg/mL BSA in buffer+6.25 μL of a 10 mg/mL $FeCl_2$ solution in water+100 μL of a 200 mM solution of ascorbic acid in water]. Following a 3 minutes incubation, 2.5 μL of substrate [50 mL Buffer+68.6 μL biotin-VBC+70.4 μL Eu (at 710 μg/mL stock)+91.6 μL Cy5CODD+50 μL of a 20 mM solution of 2-oxoglutaric acid in water+0.3 mM CHAPS] was added and incubated for 30 minutes. The plate was loaded into a PerkinElmer Viewlux for imaging. For dose response experiments, normalized data were fit by ABASE/XC50 using the equation y=a+(b−a)/(1+ (10^x/10^c)^d), where a is the minimum % activity, b is the maximum % activity, c is the $pIC_{50}$, and d is the Hill slope.

The $IC_{50}$ for exemplified compounds in the EGLN3 assay ranged from approximately 1-100 nanomolar. This range represents the data accumulated as of the time of the filing of this application. Later testing may show variations in $IC_{50}$ data due to variations in reagents, conditions and variations in the method(s) used from those given herein above. So this range is to be viewed as illustrative, and not as an absolute set of numbers.

Measure Epo Protein Produced by Hep3B Cell Line Using ELISA Method.

Hep3B cells obtained from the American Type Culture Collection (ATCC) are seeded at 2×10^4 cells/well in Dulbecco's Modified Eagle Medium (DMEM)+10% FBS in 96-well plates. Cells are incubated at 37 degC/5% CO2/90% humidity (standard cell culture incubation conditions). After overnight adherence, medium is removed and replaced with DMEM without serum containing test compound or DMSO negative control. Following 48 hours incubation, cell culture medium is collected and assayed by ELISA to quantitate Epo protein.

The $EC_{50}$ for exemplar compounds in the Hep3B ELISA assay ranged from approximately 1-20 micromolar using the reagents and under the conditions outlined herein above. This range represents the data accumulated as of the time of the filing of this initial application. Later testing may show variations in $EC_{50}$ data due to variations in reagents, conditions and variations in the method(s) used from those given herein above. So this range is to be viewed as illustrative, and not a absolute set of numbers.

These compound are believed to be useful in therapy as defined above and to not have unacceptable or untoward effects when used in compliance with a permitted therapeutic regime.

The foregoing examples and assay have been set forth to illustrate the invention, not limit it. What is reserved to the inventors is to be determined by reference to the claims.

What is claimed is:

1. A compound which is:
   N-{[1-(2-cyclopropylethyl)-4-hydroxy-2-oxo-1,2-dihydro-1,8-naphthyridin-3-yl]carbonyl}glycine;
   N-{[4-hydroxy-1-(3-methylbutyl)-2-oxo-1,2-dihydro-1,8-naphthyridin-3-yl]carbonyl}glycine;
   N-{[1-(3,3-dimethylbutyl)-4-hydroxy-2-oxo-1,2-dihydro-1,8-naphthyridin-3-yl]carbonyl}glycine;
   N-{[4-hydroxy-2-oxo-1-(phenylmethyl)-1,2-dihydro-1,8-naphthyridin-3-yl]carbonyl}glycine;
   N-({1-[2-(dimethylamino)ethyl]-4-hydroxy-2-oxo-1,2-dihydro-1,8-naphthyridin-3-yl]carbonyl}glycine;
   N-{[1-(3,3-dimethylbutyl)-4-hydroxy-7-methyl-2-oxo-1,2-dihydro-1,8-naphthyridin-3-yl]carbonyl}glycine;
   N-{[6-chloro-1-(3,3-dimethylbutyl)-4-hydroxy-2-oxo-1,2-dihydro-1,8-naphthyridin-3-yl]carbonyl}glycine;
   N-{[1-(3,3-dimethylbutyl)-4-hydroxy-2-oxo-7-(trifluoromethyl)-1,2-dihydro-1,8-naphthyridin-3-yl]carbonyl}glycine;
   N-{[1-(3,3-dimethylbutyl)-6-fluoro-4-hydroxy-2-oxo-1,2-dihydro-1,8-naphthyridin-3-yl]carbonyl}glycine;
   N-{[6-bromo-1-(3,3-dimethylbutyl)-4-hydroxy-2-oxo-1,2-dihydro-1,8-naphthyridin-3-yl]carbonyl}glycine;
   N-[(1-{[4-(1,1-dimethylethyl)phenyl]methyl}-6-fluoro-4-hydroxy-2-oxo-1,2-dihydro-1,8-naphthyridin-3-yl)carbonyl]glycine;
   {[6-{[(carboxymethyl)amino]carbonyl}-8-(3,3-dimethylbutyl)-5-hydroxy-2-methyl-7-oxo-7,8-dihydro-1,8-naphthyridin-4-yl]amino}acetic acid;
   N-[(1-{[4-(1,1-dimethylethyl)phenyl]methyl}-4-hydroxy-2-oxo-1,2-dihydro-1,8-naphthyridin-3-yl)carbonyl]glycine;
   N-{[1-{[4-(1,1-dimethylethyl)phenyl]methyl}-4-hydroxy-2-oxo-7-(trifluoromethyl)-1,2-dihydro-1,8-naphthyridin-3-yl]carbonyl}glycine;
   N-({1-[(2-chlorophenyl)methyl]-4-hydroxy-2-oxo-1,2-dihydro-1,8-naphthyridin-3-yl]carbonyl}glycine;
   or a pharmaceutically acceptable salt thereof.

2. A pharmaceutical composition comprising a compound of claim 1 or a pharmaceutically acceptable salt thereof and one or more of pharmaceutically acceptable carriers, diluents or excipients.

* * * * *